(12) United States Patent
Henderson

(10) Patent No.: US 7,339,306 B2
(45) Date of Patent: *Mar. 4, 2008

(54) MECHANISM COMPRISED OF ULTRASONIC LEAD SCREW MOTOR

(75) Inventor: David Henderson, Victor, NY (US)

(73) Assignee: New Scale Technologies Inc., Victor, NY (US)

( * ) Notice: Subject to any disclaimer, the term of this patent is extended or adjusted under 35 U.S.C. 154(b) by 135 days.

This patent is subject to a terminal disclaimer.

(21) Appl. No.: 10/918,041

(22) Filed: Aug. 13, 2004

(65) Prior Publication Data

US 2005/0052098 A1    Mar. 10, 2005

Related U.S. Application Data

(63) Continuation-in-part of application No. 10/657,325, filed on Sep. 8, 2003, now Pat. No. 6,940,209.

(51) Int. Cl.
*H01L 41/08* (2006.01)

(52) U.S. Cl. .................................. 310/323.02

(58) Field of Classification Search ........... 310/323, 310/318, 323.02, 323.09, 323.08
See application file for complete search history.

(56) References Cited

U.S. PATENT DOCUMENTS

| | | | |
|---|---|---|---|
| 2,439,499 A | 4/1948 | Williams | |
| 3,176,167 A | 3/1965 | Vosseler | |
| 3,582,540 A | 6/1971 | Adler | |
| 3,612,664 A | 10/1971 | Berman | |
| 3,736,532 A | 5/1973 | Armenakas | |
| 3,902,084 A | 8/1975 | May, Jr. | |
| 3,958,117 A | 5/1976 | Stauffer | |
| 4,184,759 A | 1/1980 | Ito | |
| 4,236,794 A | 12/1980 | Gordon | |
| 4,277,948 A | 7/1981 | Horn | |
| 4,352,300 A | 10/1982 | Esch | |
| 4,354,203 A | 10/1982 | Koyama | |
| 4,482,828 A | 11/1984 | Vergues et al. | |
| 4,629,308 A | 12/1986 | Landa | |
| 4,734,610 A | 3/1988 | Okumura | |

(Continued)

FOREIGN PATENT DOCUMENTS

DE    2815391 A    10/1979

(Continued)

OTHER PUBLICATIONS

Bolt Science, "Vibration Loosening of Bolts and Threaded Fasteners," at http://www.boltscience.com/pages/vibloose.htm (accessed Nov. 29, 2006).

(Continued)

*Primary Examiner*—Darren Schuberg
*Assistant Examiner*—Karen Beth Addison
(74) *Attorney, Agent, or Firm*—Nixon Peabody LLP

(57) ABSTRACT

An optical assembly that contains an optical device movably attached to a apparatus for driving a threaded shaft assembly. The apparatus contains of a threaded shaft with an axis of rotation and, engaged therewith, a threaded nut. The assembly contains a device for subjecting the threaded nut to ultrasonic vibrations and thereby causing said the shaft to simultaneously rotate and translate in the axial direction.

20 Claims, 39 Drawing Sheets

U.S. PATENT DOCUMENTS

| | | | |
|---|---|---|---|
| 4,757,223 A | 7/1988 | Ueyama | |
| 4,776,156 A | 10/1988 | Brown | |
| 4,781,053 A | 11/1988 | Stewart | |
| 4,857,791 A | 8/1989 | Uchino et al. | |
| 4,871,240 A | 10/1989 | Suda | |
| 4,994,698 A | 2/1991 | Kliman | |
| 5,036,245 A | 7/1991 | Ohnishi | |
| 5,045,747 A | 9/1991 | Chen | |
| 5,091,781 A | 2/1992 | An | |
| 5,127,982 A | 7/1992 | Kotake | |
| 5,134,334 A | 7/1992 | Onlshi | |
| 5,144,187 A * | 9/1992 | Culp | 310/323.02 |
| 5,157,435 A | 10/1992 | Min | |
| 5,211,101 A | 5/1993 | Letsch | |
| 5,237,234 A | 8/1993 | Jebens et al. | |
| 5,237,236 A * | 8/1993 | Culp | 310/323.02 |
| 5,296,943 A | 3/1994 | Goebel | |
| 5,316,319 A | 5/1994 | Suggs | |
| 5,357,308 A | 10/1994 | Goo | |
| 5,387,835 A * | 2/1995 | Tsukimoto et al. | 310/323.13 |
| 5,398,163 A | 3/1995 | Sano | |
| 5,408,332 A | 4/1995 | Murakami et al. | |
| 5,410,206 A | 4/1995 | Luecke | |
| 5,426,336 A | 6/1995 | Jacobsen et al. | |
| 5,434,621 A | 7/1995 | Yu | |
| 5,446,330 A | 8/1995 | Eda | |
| 5,453,653 A | 9/1995 | Zumeris | |
| 5,461,442 A | 10/1995 | Ohshita | |
| 5,528,429 A | 6/1996 | Hagimori | |
| 5,605,659 A | 2/1997 | Moynihan | |
| 5,635,782 A | 6/1997 | Jacobsen et al. | |
| 5,654,757 A | 8/1997 | Murakami et al. | |
| 5,663,606 A | 9/1997 | Beurrier | |
| 5,739,624 A | 4/1998 | Kleiman | |
| 5,739,626 A | 4/1998 | Kojima | |
| 5,763,983 A | 6/1998 | Huang | |
| 5,769,554 A | 6/1998 | Slocum | |
| 5,774,282 A | 6/1998 | Kohmoto et al. | |
| 5,792,379 A | 8/1998 | Dai | |
| 5,814,917 A | 9/1998 | Isobe | |
| 5,894,371 A | 4/1999 | Wrobel | |
| 5,917,158 A | 6/1999 | Takao et al. | |
| 5,943,513 A | 8/1999 | Kim | |
| 5,966,248 A | 10/1999 | Kurokawa et al. | |
| 5,969,886 A | 10/1999 | Sato | |
| 5,982,075 A | 11/1999 | Hayasaka | |
| 6,101,840 A | 8/2000 | Watanabe | |
| 6,125,701 A | 10/2000 | Sugitani | |
| 6,142,749 A | 11/2000 | Jack | |
| 6,145,805 A | 11/2000 | Smith, III | |
| 6,147,435 A | 11/2000 | Fujimura | |
| 6,170,202 B1 | 1/2001 | Davoodi | |
| 6,236,448 B1 | 5/2001 | Ota | |
| 6,257,845 B1 | 7/2001 | Jack | |
| 6,308,113 B1 | 10/2001 | Nowlin et al. | |
| 6,311,020 B1 | 10/2001 | Torikoshi | |
| 6,321,016 B1 | 11/2001 | Tirloni et al. | |
| 6,325,351 B1 | 12/2001 | Hale | |
| 6,366,004 B1 * | 4/2002 | Yano et al. | 310/323.08 |
| 6,430,369 B2 | 8/2002 | Lee et al. | |
| 6,439,282 B1 | 8/2002 | Kimura | |
| 6,445,514 B1 | 9/2002 | Ohnstein | |
| 6,483,713 B2 | 11/2002 | Samant et al. | |
| 6,525,456 B1 | 2/2003 | Kim | |
| 6,532,331 B1 | 3/2003 | Kato et al. | |
| 6,548,926 B2 | 4/2003 | Dobson | |
| 6,591,608 B2 | 7/2003 | Langenfeld | |
| 6,606,426 B2 | 8/2003 | Laor | |
| 6,664,711 B2 | 12/2003 | Baudendistel | |
| 6,678,240 B2 | 1/2004 | Geh | |
| 6,799,483 B2 | 10/2004 | Petri | |
| 6,911,763 B2 | 6/2005 | Ziegler et al. | |
| 6,927,344 B1 | 8/2005 | Gall et al. | |
| 6,940,209 B2 * | 9/2005 | Henderson | 310/323.02 |
| 6,949,836 B2 | 9/2005 | Oya | |
| 6,954,985 B2 | 10/2005 | Lee et al. | |
| 6,983,667 B2 | 1/2006 | Cuerden et al. | |
| 7,170,214 B2 | 1/2007 | Henderson et al. | |
| 2002/0187020 A1 | 12/2002 | Julien | |
| 2003/0049095 A1 | 3/2003 | Boyer | |
| 2004/0126074 A1 | 7/2004 | Bickham et al. | |
| 2005/0063663 A1 | 3/2005 | Anderson et al. | |
| 2005/0185906 A1 | 8/2005 | Bickham et al. | |
| 2006/0049720 A1 | 3/2006 | Henderson et al. | |

FOREIGN PATENT DOCUMENTS

| | | |
|---|---|---|
| DE | 3303745 A | 8/1984 |
| JP | 919131 | 1/1997 |
| SU | 529063 A | 4/1977 |
| SU | 597548 A | 3/1978 |
| SU | 954203 A | 9/1982 |
| SU | 977144 A | 11/1982 |

OTHER PUBLICATIONS

Holland & Tran, "Finite Element Modelling of Threaded Fastener Loosening Due to Dynamic Forces," Proceeding of the 8th International Conference on the Application of Artificial Intelligence to Civil and Structural Engineering Computing, Stirling, Scotland, pp. 125-126 (2001) (abstract only).

Arnot Q, Custom Cues, "The Arnot Q Euro Custom Cue. Purchased by Gerherdt Junker," at http://arnotq.com/pages/60/60.html (Google Cache Search "Gerhardt Junker" accessed Sep. 23, 2006).

Zadoks & Yu, "An Investigation of the Self-Loosening Behavior of Bolts Under Transverse Vibration," *Journal of Sound and Vibration* 208(2):189-209 (1997) (abstract only).

Sybil P. Parker, "McGraw-Hill Dictionary of Scientific and Technical Terms," 1989, p. 1253, 4th Edition, McGraw-Hill Book Company. New York, U.S.A.

Eugene A. Avallone et al., "Mark's Standard Handbook for Mechanical Engineers," 1978, p. 5-59 to 5-70, 9th Edition, McGraw-Hill Book Company, New York, U.S.A.

Eugene A. Avallone et al., "Mark's Standard Handbook for Mechanical Engineers," 1978, p. 8-9 to 8-90, 9th Edition, McGraw-Hill Book Company, New York, U.S.A.

Petri, Patrick "Vibration-Induced Rotation", Massachusetts Institute of Technology, Department of Mechanical Engineering, May 14, 2001 (56 pages).

Vinogradov et al. "On a High Frequency Mechanism of Self-loosening of Fasteners", American Society of Mechanical Engineers, Design Engineering Division (Publication) DE Publ. by American Society of Mechanical Engineers (ASME), New York NY USA 18-4, pp. 131-137 (1989) (7 pages).

Fujita et al., "A threaded Wobble Motors. A Micro Generating Large Linear Displacement", The 8th International conference on Solid-State Sensors and Actuators, and Eurosensors IX, Stockholm, Sweden, Jun. 25-29, 1995, pp. 408-411 (4 pages).

Hess and Sudhirkashyap, "Dynamic Loosening and Tightening of a Single-Bolt Assembly," Journal of Vibration and Acoustics 119(3): 311-16 (1997).

\* cited by examiner

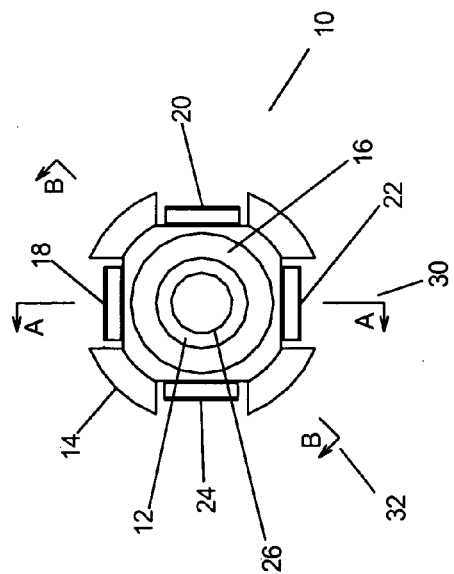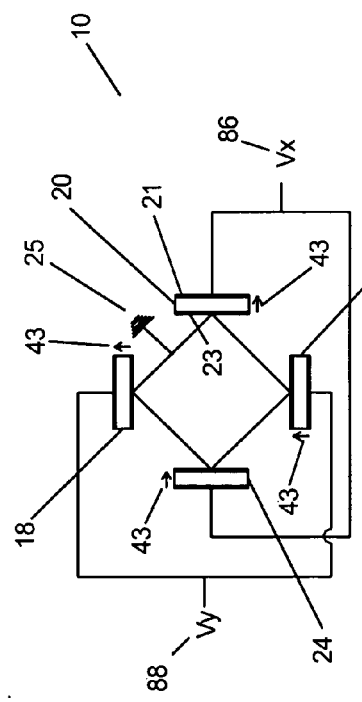

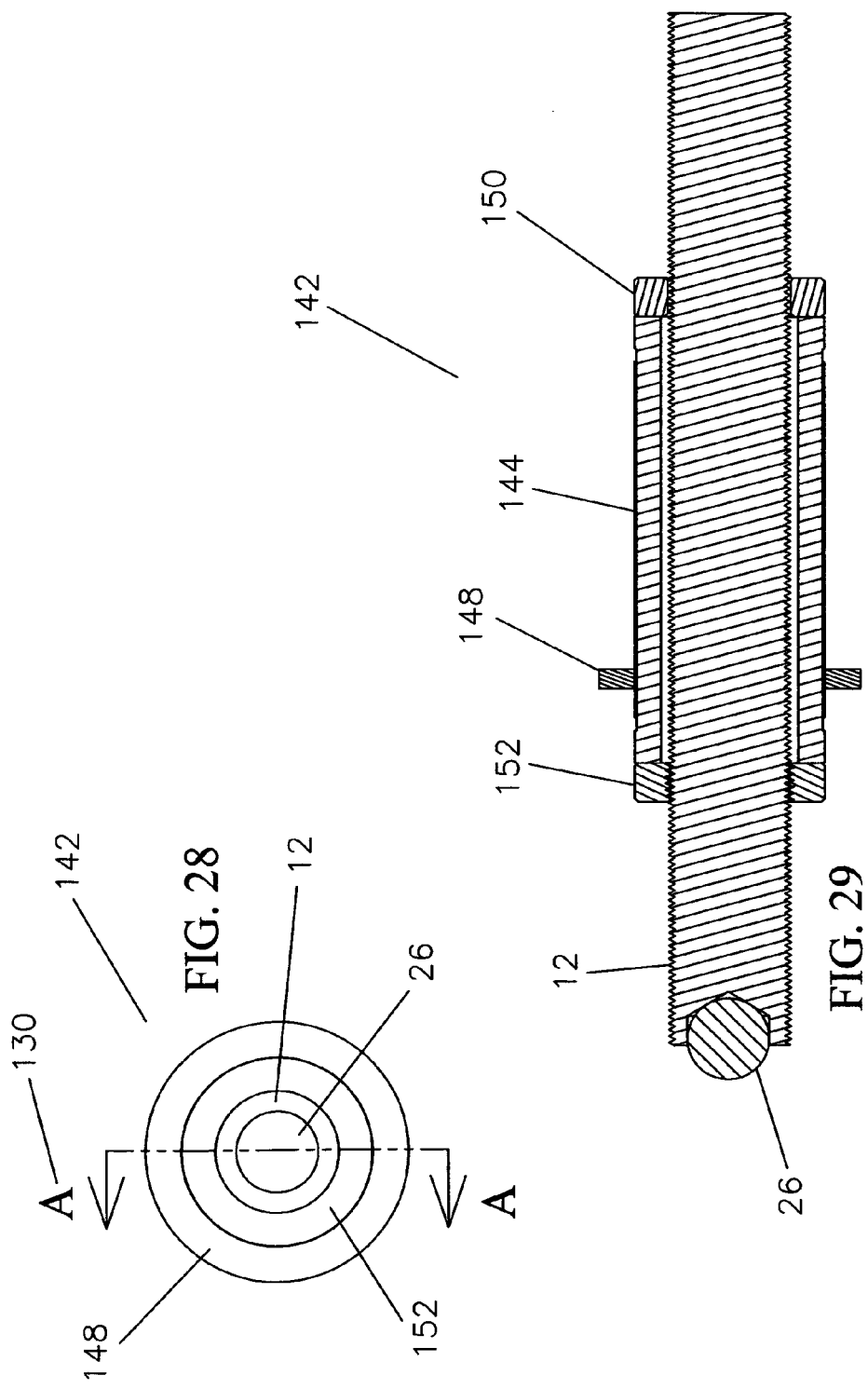

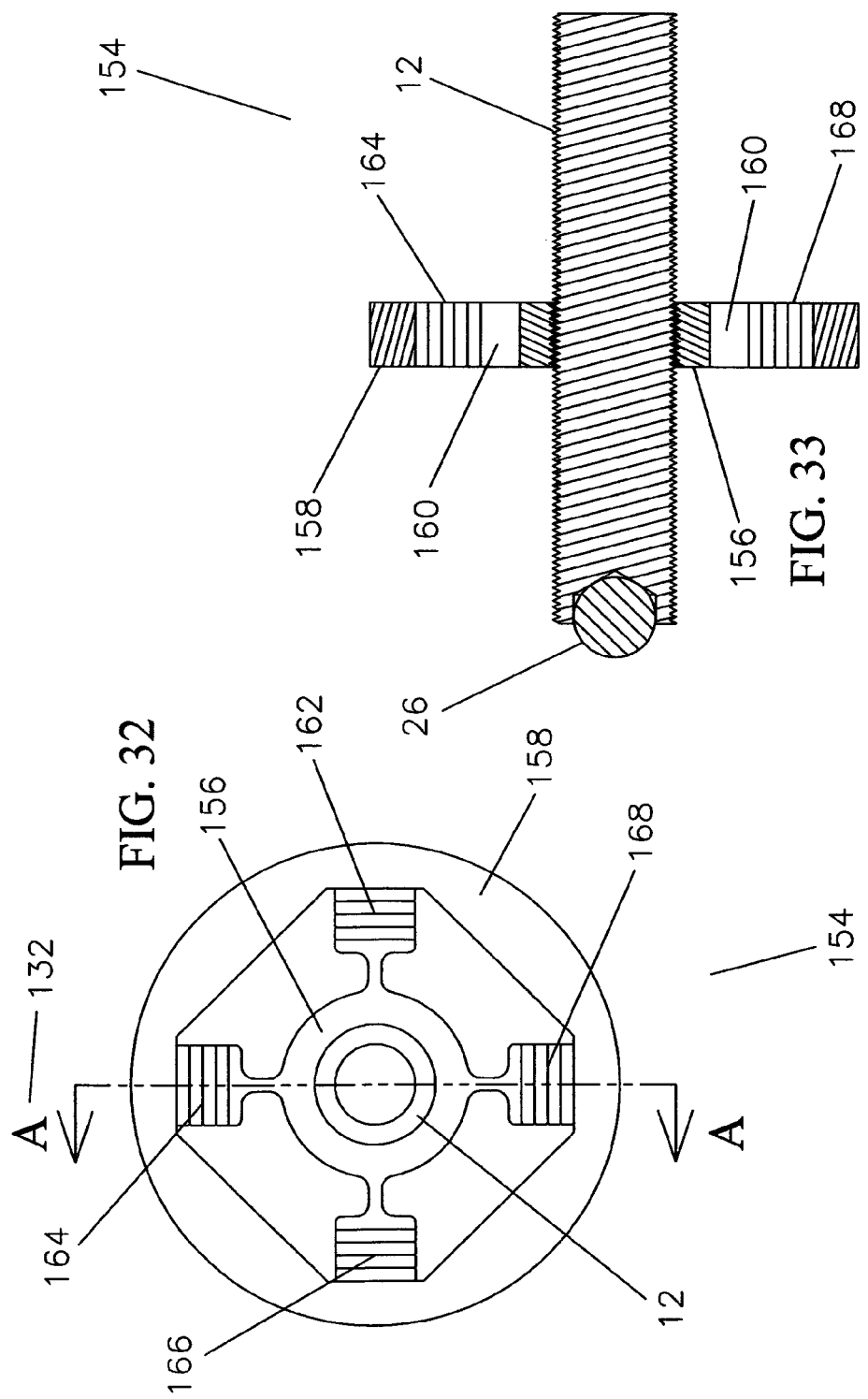

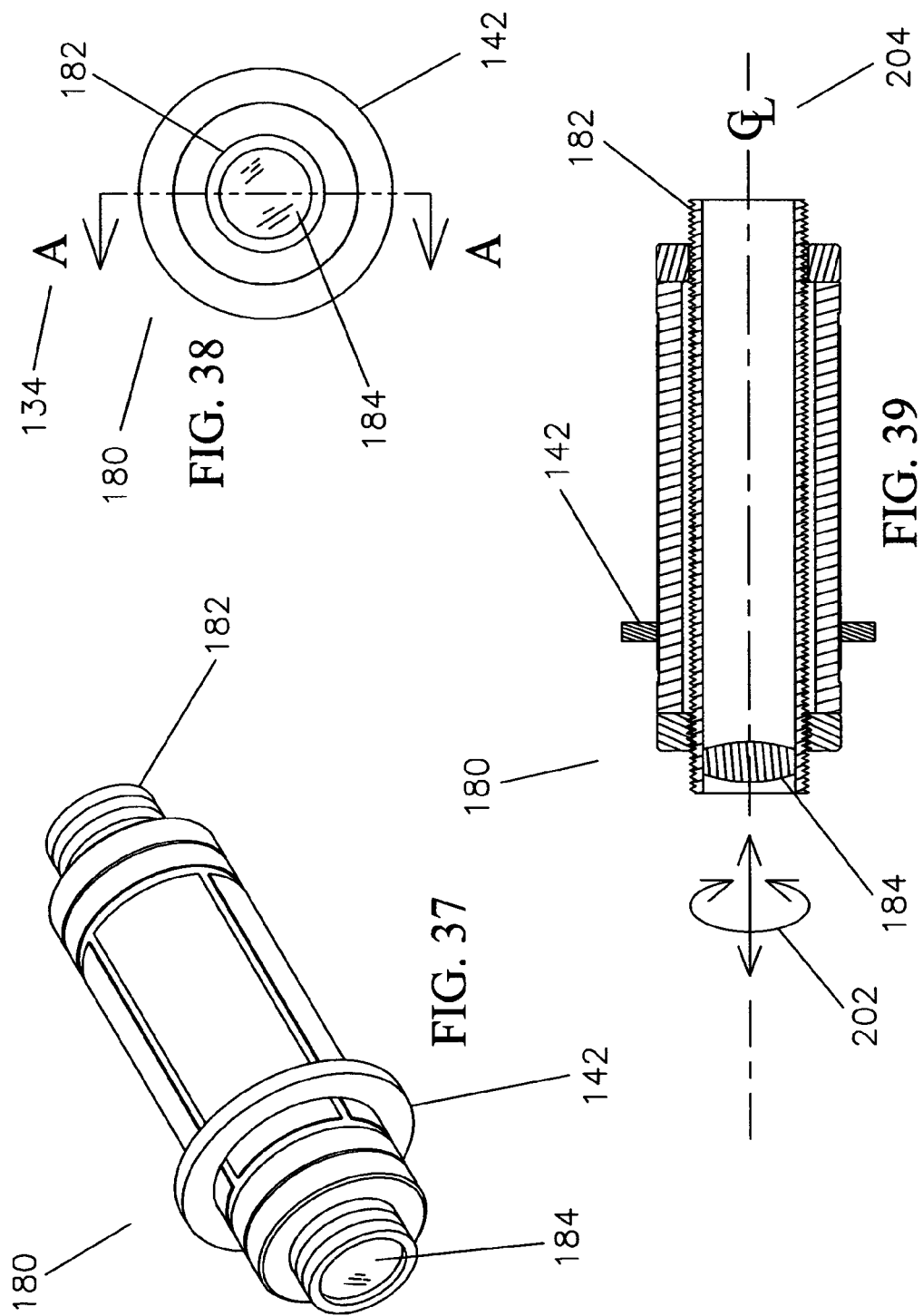

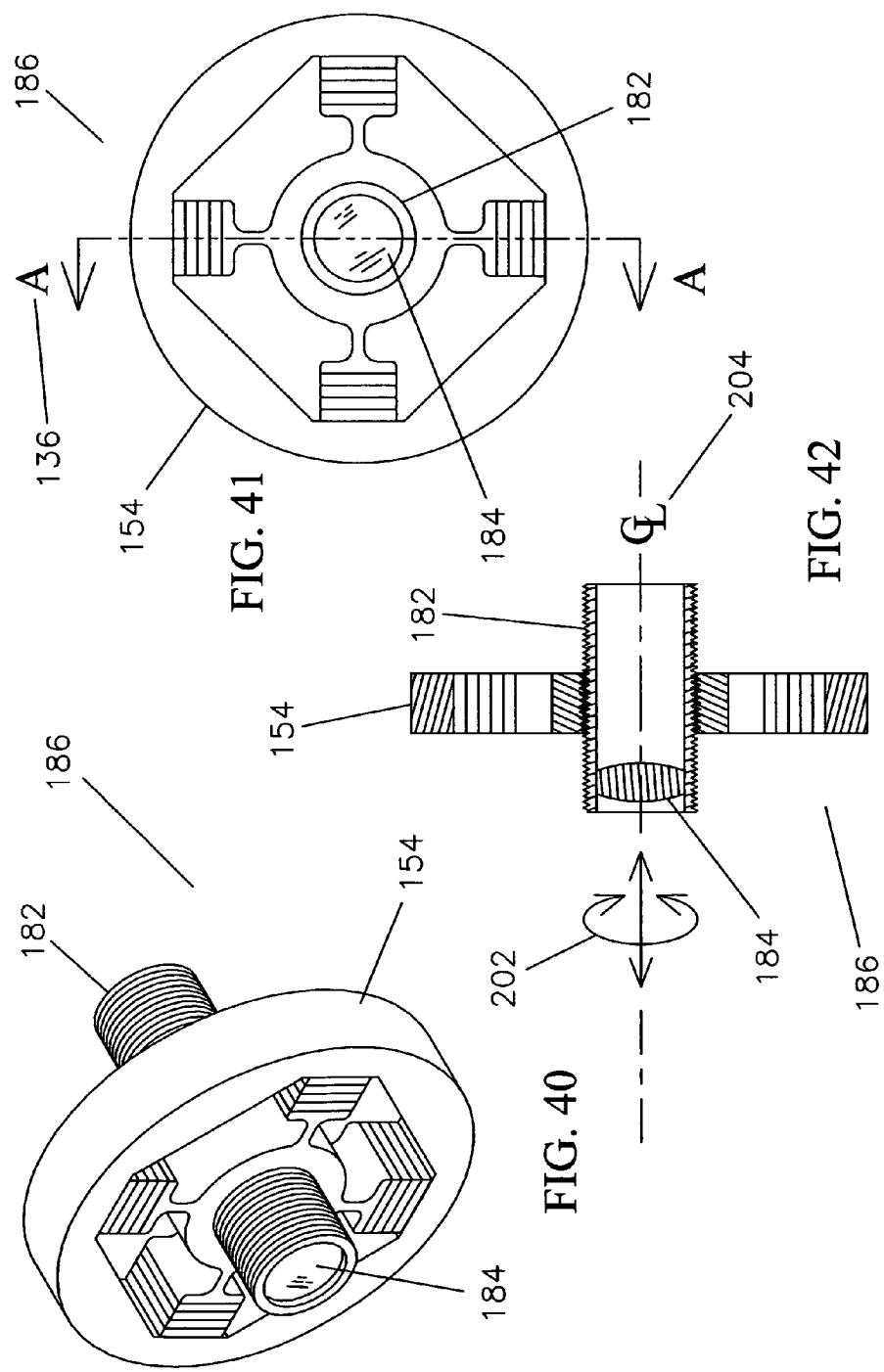

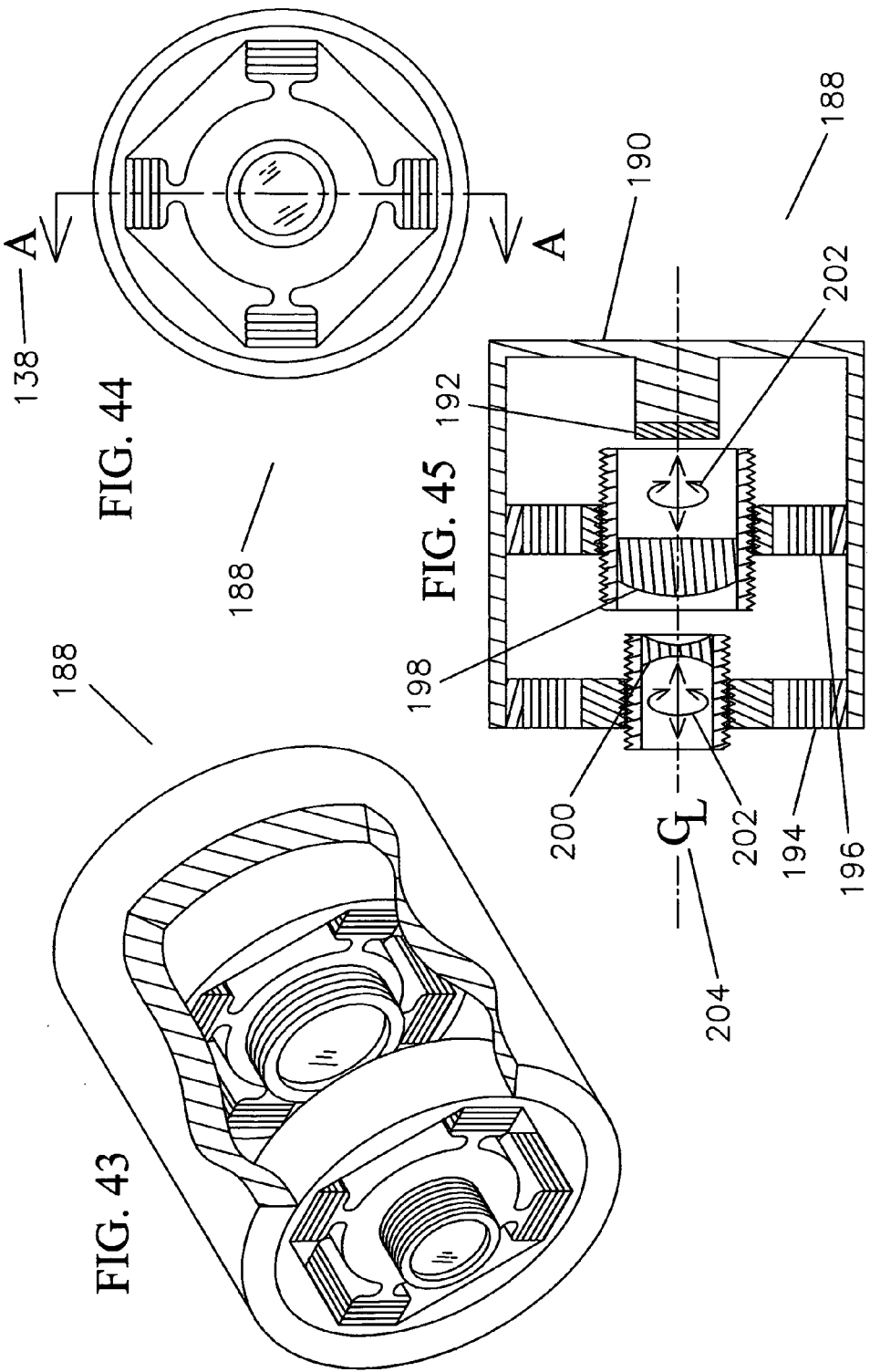

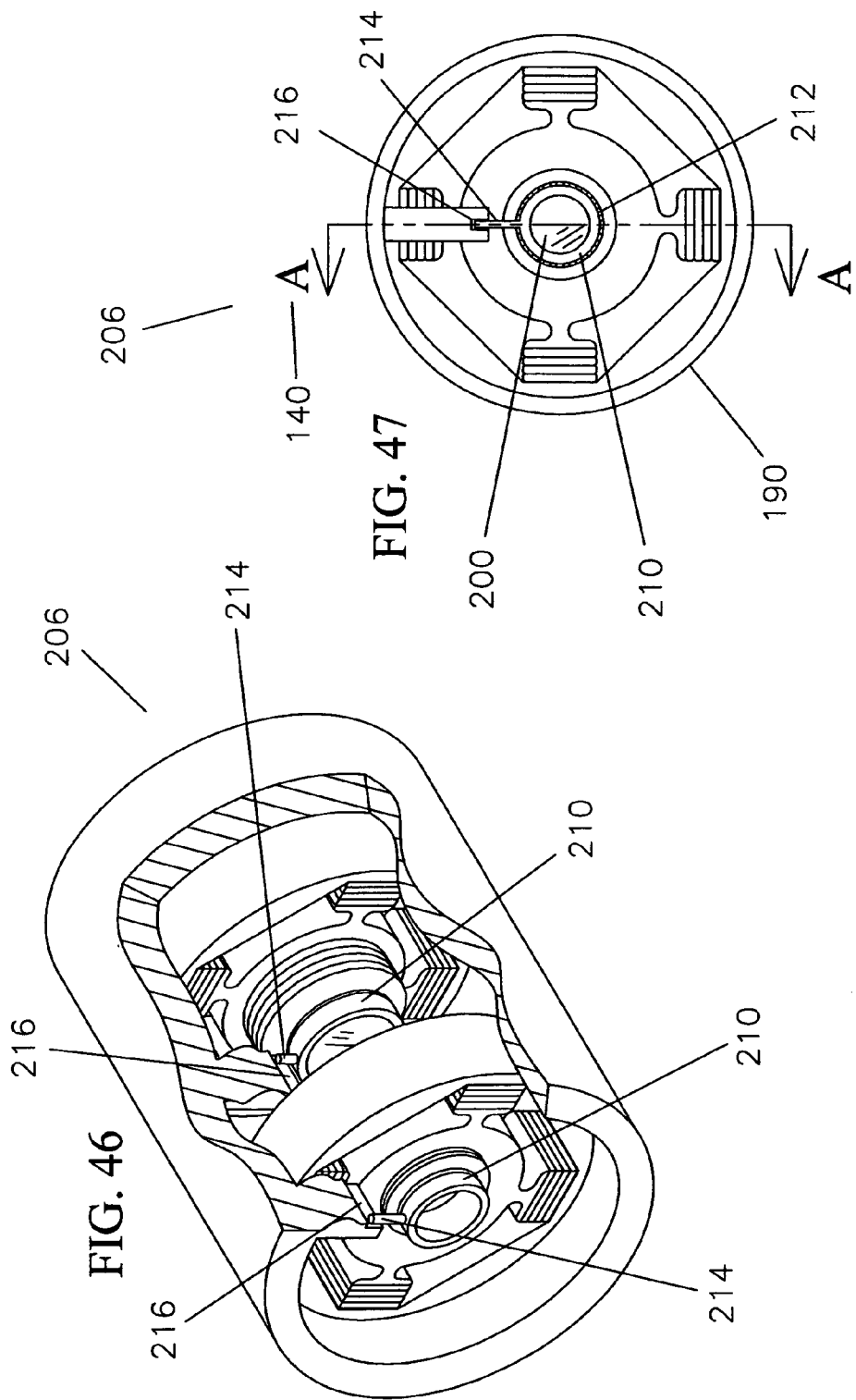

MECHANISM COMPRISED OF ULTRASONIC LEAD SCREW MOTOR

CROSS-REFERENCE TO RELATED PATENT APPLICATIONS

This application is a continuation-in-part of applicant's application U.S. Ser. No. 10/657,325, filed on Sep. 8, 2003 now U.S. Pat. No. 6,940,209.

FIELD OF THE INVENTION

An imaging device that contains a miniature ultrasonic linear motor assembly comprised of a threaded shaft and, engaged, therewith, a nut.

BACKGROUND OF THE INVENTION

Transducers using piezoelectric electrostrictive, electrostatic, or electromagnetic technologies are very useful for precise positioning at the nanometer scale. In the case of a piezoelectric device, the ceramic is formed into a capacitor that changes shape when charged and discharged creating a force transducer or position actuator. When used as a position actuator, the shape change of the piezoelectric ceramic is approximately proportional to the applied voltage. Piezoelectric actuators are limited in range to about 0.1 percent of the length of the ceramic which corresponds to typical stroke lengths of tens of micrometers. While the high stiffness and nanometer precision of piezoelectric actuators is very useful, more stroke is needed for many applications.

Numerous piezoelectric motor designs have been developed to "rectify" small ceramic shape changes and generate longer stroke.

A PZT stepping motor is described in U.S. Pat. No. 3,902,084; the entire disclosure of this U.S. patent is hereby incorporated by reference into this specification. This motor uses a clamp-extend-clamp-retract operating sequence to add together many short PZT actuator cycles. This stepping linear actuator operates at frequencies from DC to several kilohertz, which produces loud noise and vibration. Position is not maintained when power is off. Resolution better than one nanometer is achieved over 200 millimeters of travel.

A PZT inertial stick-slip motor is described in U.S. Pat. No. 5,410,206; the entire disclosure of this U.S. patent is hereby incorporated by reference into this specification. This motor rotates a fine-threaded shaft using a split nut, which forms "jaws" that grip the shaft on opposite sides. A PZT actuator rapidly moves the jaws in opposite directions with an asymmetric alternating current drive signal. Fast jaw movements overcome the clamping friction and create slippage. Slower jaw movements do not slip and rotate the shaft. This stick-slip motor makes similar noise and vibration as the above stepping motor but moves 100 times slower and holds position when power is turned off. Resolution better than 50 nanometers is achieved over 25 millimeters of travel.

Ultrasonic motors use piezoelectric-generated vibrations to create continuous movement with high speed, high torque, small size and quiet operation.

One of the earliest ultrasonic piezoelectric motors is described in U.S. Pat. No. 3,176,167; the entire disclosure of this United States patent is hereby incorporated by reference into this specification. This unidirectional rotary motor uses a quartz crystal oscillator to move a thin rod and drive a ratchet wheel with the objective of driving a clock mechanism.

An example of a standing wave ultrasonic motor is described in U.S. Pat. No. 5,453,653; the entire disclosure of this United States patent is hereby incorporated by reference into this specification. This motor uses a rectangular PZT plate to generate ultrasonic oscillations of a contact point that is preloaded against a moving surface. The electrode pattern on the PZT plate is connected to an alternating current signal and generates two-dimensional oscillations of the contact tip with the required amplitude and phase to generate a net force against the mating surface. This ultrasonic motor is quiet and 100 times faster than a stepping motor while producing about one third of the force. Generally ultrasonic motors are difficult to stop and start which limits precision. An encoder with closed-loop control is typically required to achieve sub-micrometer resolution.

A device for driving a threaded rod using ultrasonic vibrations is described, e.g., in U.S. Pat. No. 6,147,435 of Katsuyuki Fujimura; the entire disclosure of this patent is hereby incorporated by reference into this specification. This patent discloses and claims: " . . . A mechanism for driving a screw rod by supersonic vibration, comprising: a screw rod provided with a groove portion formed helically along an axial direction thereof; a pair of stands rotatably holding opposite ends of said screw rod; a work rack partially surrounding said screw rod and slidable in the axial direction of said screw rod; at least one first screw rod rotation device secured on one side of said work rack and extending from said work rack to said screw rod, said at least one first screw rod rotation device comprising a first vibrator contacting with said groove portion of said screw rod at a first specific angle, a first spring urging said first vibrator toward said groove portion of said screw rod at a specific pressure and a first piezoelectric actuator for vibrating said first vibrator upon electrical activation to rotate said screw rod in a first rotational direction; and at least one second screw rod rotation device secured on another side of said work rack and extending from said work rack to said screw rod, said at least one second screw rod rotation device comprising a second vibrator contacting with said groove portion of said screw rod at a second specific angle opposite said first specific angle, a second spring urging said second vibrator toward said groove portion of said screw rod at a specific pressure and a second piezoelectric actuator for vibrating said second vibrator upon electrical activation to rotate said screw rod in a second direction."

The device of U.S. Pat. No. 6,147,435 requires both a "first screw rod rotation device" and a "second screw rod rotation device"; these are illustrated in FIG. 3, e.g., as elements 16a' and 16d' (which comprise such first screw rod rotation device), and as elements 16b' and 16c' (which comprise such second screw rod rotation device.) Referring again to U.S. Pat. No. 6,147,435, when elements 16a' and 16d' are activated by ultrasonic vibration, the screw rod 2 is caused to rotate in one direction; and when elements 16b' and 16c' are activated by ultrasonic vibration, the screw rod 2 is caused to rotate in the opposite direction.

The elements 16a'/16d', and 16b'/16c' are never activated simultaneously; to do so would waste energy and cause the screw rod 2 to remain stationary.

However, even when such elements 16a'/16d' and 16b'/16c' are not activated simultaneously, there is a waste of energy. The inactive pair of elements still are contiguous with the threads on screw rod 2 and, thus, cause drag friction.

This drag friction is a problem with the device of U.S. Pat. No. 6,147,435. As is described in claim 2 of the patent, and in order to somewhat solve this problem, with the device of such patent " . . . when one of said first and second piezoelectric actuators is electrically activated, a very small amount of electric current is supplied to the other of said first and second piezoelectric actuators." The efficiency of the device of U.S. Pat. No. 6,147,435 is not very high.

It is an object of this invention to provide a mechanism for driving a threaded shaft by ultrasonic vibration that has a substantially higher efficiency than that of U.S. Pat. No. 6,147,435 while providing higher precision, force, and speed than is typically achieved by other ultrasonic motors of a similar size.

It is another object of this invention to provide an imaging device comprised of the aforementioned mechanism for driving a threaded shaft.

SUMMARY OF THE INVENTION

In accordance with this invention, there is provided an optical assembly comprised of an optical element connected to an apparatus for driving a threaded shaft assembly, wherein said apparatus for driving a threaded shaft assembly is comprised of a threaded shaft and, engaged therewith, a nut. The assembly contains means for subjecting said nut to ultrasonic vibration and thereby causing said shaft to simultaneously rotate and translate in the axial direction. The assembly also is comprised of means for applying an axial force upon said shaft.

BRIEF DESCRIPTION OF THE DRAWINGS

The invention will be described by reference to this specification, the appended claims, and the drawings, wherein like numerals refer to like element, and wherein:

FIGS. 1 through 6 show a motor containing four rectangular piezoelectric plates wherein FIG. 1 is a perspective view of such motor, FIG. 2 is an exploded view of such motor, FIG. 3 is an end view of such motor, FIG. 4 shows the electrical connections to such motor, FIG. 5 is cross sectional view of motor taken along lines A-A (30) of FIG. 3, FIG. 6 is a cross section view taken along lines B-B (32) of FIG. 3;

FIGS. 7 through 12 illustrate a motor containing four piezoelectric stacks wherein: FIG. 7 is a perspective view of such motor, FIG. 8 is an exploded view of such motor, FIG. 9 is an end view of such motor, FIG. 10 shows the electrical connections to such motor, FIG. 11 is cross section view taken along lines A-A (48) of FIG. 9, and FIG. 12 is cross section view taken along lines B-B (46) of FIG. 9;

FIGS. 13 through 17 illustrate a motor containing a piezoelectric tube with four outer electrodes wherein: FIG. 13 is a perspective view of such motor, FIG. 14 is an exploded view of such motor, FIG. 15 is an end view of such motor, FIG. 16 shows the electrical connections to such motor, FIG. 17 is cross sectional view taken along lines A-A (56) of FIG. 15;

FIG. 20 through 25 show applications of the motor of FIG. 1 packaged and integrated with linear stages, wherein: FIG. 20 is a perspective view of the motor assembly, FIG. 21 is an exploded view of the motor assembly, FIG. 22 is a cross section view of the motor assembly, FIG. 24B shows the motor assembly integrated in a linear stage operating in the reverse direction and FIG. 25 shows the motor assembly integrated in a three-axis stage system;

FIGS. 26 through 29 illustrate a motor containing a piezoelectric tube with four outer electrodes which is similar to FIGS. 13 through 17 wherein: FIG. 26 is a perspective view of such motor, FIG. 27 is an exploded view of such motor, FIG. 28 is an end view of such motor, FIG. 29 is cross sectional view taken along lines A-A (130) of FIG. 28.

FIGS. 30 through 36 illustrate a motor containing four piezoelectric stacks in a planar arrangement wherein: FIG. 30 is a perspective view of such motor, FIG. 31 is an exploded view of such motor, FIG. 32 is an end view of such motor, FIG. 33 is cross section view taken along lines A-A (132) of FIG. 32, FIG. 34 shows the electrical connections to a singlepiezoelectric stack in such motor, FIG. 35 shows the electrical connections to the four stacks insuch motor, and FIG. 36 is a schematic illustration of the orbital movement of threaded nut for such motor of FIG. 30 showing the rotation of the threaded shaft, which is similar to the dynamic operation shown in FIG. 18.

FIGS. 37 through 41 illustrate an optical alignment mechanism integrating a motor and lens wherein: FIG. 37 is a perspective view of the motor in FIG. 26 with a hollow shaft with a lens installed inside said shaft, FIG. 38 is an end view of such motor, FIG. 39 is a cross section view taken along lines A-A (134) of FIG. 38, FIG. 40 is a perspective view of the motor in FIG. 30 with a hollow shaft with a lens installed inside said shaft, FIG. 41 is an end view of such motor, and FIG. 42 is a cross section view taken along lines A-A (136) of FIG. 41;

FIGS. 43 through 45 illustrate a camera auto focus and auto zoom assembly integrating two optical alignment mechanisms shown in FIG. 40 with an focal plane imaging device wherein: FIG. 43 is a perspective view of the camera assembly, FIG. 44 is an end view of such assembly, and FIG. 45 is a cross section view taken along lines A-A (138) of FIG. 44; and FIGS. 46 through 48 illustrate a camera assembly, as shown in FIG. 43, where the optical lens are mounted on bearings with anti-rotation pins so that the lens translate but do not rotate wherein: FIG. 46 is a perspective view of the camera assembly, FIG. 47 is an end view of such assembly, and FIG. 48 is a cross section view taken along A-A (140) of FIG. 47.

DESCRIPTION OF THE PREFERRED EMBODIMENTS

Figure 1:
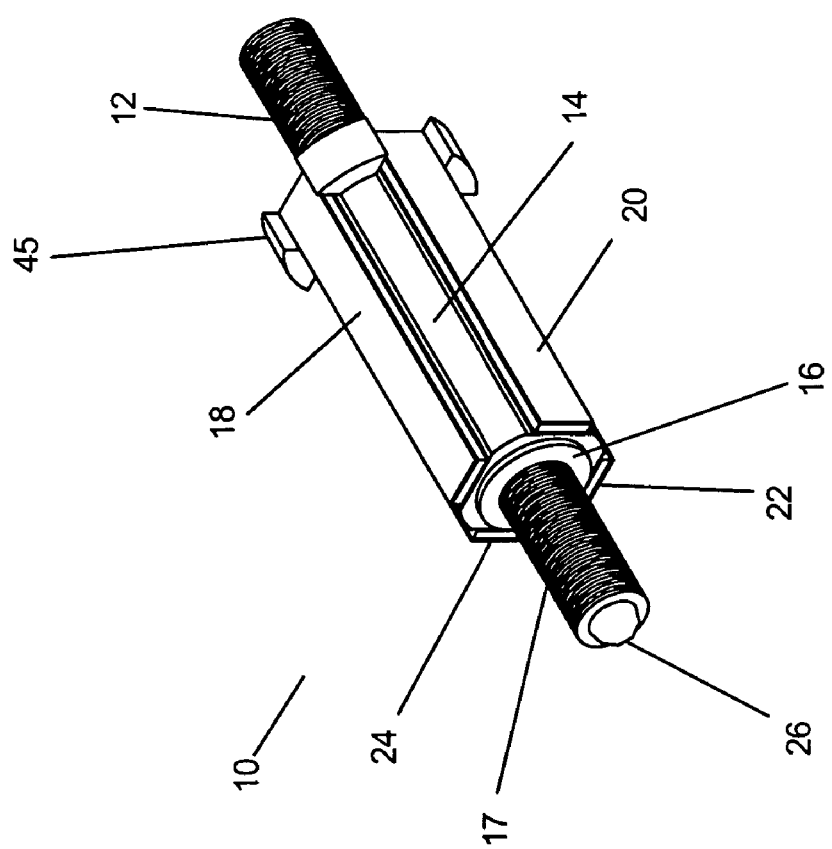

In the first part of this specification, applicant will describe a miniature ultrasonic linear motor. In the second part of this specification, applicant will describe an optical assembly comprised of an optical device connected to such motor.

In one embodiment of this invention, a miniature ultrasonic linear motor rotates a lead screw to produce linear movement. A cylinder supports a threaded nut with a first bending mode resonant frequency in the ultrasonic range. The cylinder and nut are excited at this resonant frequency by transducers that cause the nut to orbit at the end of the cylinder. The transducers may be piezoelectric, electrostrictive, electrostatic, electromagnetic or any device that can stimulate the resonant vibration. At least two transducers are required to simultaneously excite the orthogonal bending modes of the cylinder with a plus or minus 90-degree phase shift and create a circular orbit. A close-fitting threaded shaft is installed inside the nut. A resilient axial load is applied to the shaft through a low friction coupling. The nut orbits at its resonant frequency, and the shaft's inertia keeps it centered. The orbit of the nut generates torque that rotates the shaft and creates linear movement. At least two alternating current drive signals are required for the transducers. The drive frequency must excite the mechanical frequency and control phase to achieve a circular nut orbit. Modulation of drive signal amplitude and duration control velocity. Phase shift between the drive signals may be positive or negative, which reverses the direction of the nut orbit and the shaft rotation/translation. This embodiment, and other preferred embodiments, will be described in greater detail in the remainder of this specification.

Without wishing to be bound to any particular theory, applicant believes that the operating principle of one of his ultrasonic linear actuators is the excitation of the first bending resonance of a cylindrical tube, which causes one or both ends of the tube to orbit around the cylindrical axis without rotating. In this embodiment, one end of the tube houses a threaded nut that also orbits around a mating threaded shaft and imparts a tangential force via friction thus rotating the threaded shaft as it orbits. The friction in the threads is helpful because it directly drives the screw. This is in strong contrast to conventional lead screw drives, where the thread contact friction is parasitic and creates windup, backlash and slow response. Another significant advantage of helical threads used in this embodiment is the direct conversion of rotation to translation with large mechanical advantage, which magnifies axial force and reduces linear speed and, as a result, increases precision.

In this embodiment, a transducer both either within or outside of the load path is preferably used to excite the first bending mode. Examples of transducers that can be used are, e.g., piezoelectric elements and stacks, magnetostrictive materials, and electrostatic materials to name a few. This list does not include all transducer materials, but it should be understood that any such material or mechanism that could be used to excite the first bending resonance of a cylindrical tube or similarly shaped block and achieve the orbit of one or both tube ends is embodied in this patent. The embodiments described herein use piezoelectric material but could just as easily be embodied with an alternate transducer material described above.

Referring to FIGS. 1 through 6, and in the preferred embodiment depicted therein, an ultrasonic linear motor 10 is depicted. In the embodiment depicted, four rectangular piezoelectric plates are used to generate ultrasonic vibrations. In another embodiment, not shown in FIG. 1, other means may be used to generate ultrasonic vibrations.

As used in this specification, the term ultrasonic refers to an operating frequency in excess of 20,000 Hertz. In one embodiment, the operating frequency is at least about 25,000 Hertz. In another embodiment, the operating frequency is at least about 50,000 Hertz. In yet another embodiment, the operating frequency is at least about 100,000 Hertz.

As used in this specification, the term linear motor refers an actuator that produces movement in a substantially straight line by generating force and/or displacement. Reference may be had, e.g., to U.S. Pat. Nos. 5,982,075 (ultrasonic linear motor), 5,134,334 (ultrasonic linear motor), 5,036,245 (ultrasonic linear motor), 4,857,791 (linear motor), and the like. The entire disclosure of each of these United States patents is hereby incorporated by reference into this specification.

Referring again to FIGS. 1 through 6, and in the preferred embodiment depicted therein, it will be seen that a threaded shaft 12 with a spherical ball tip 26 rotates and produces axial force and motion The threaded shaft 12 is preferably movably disposed within a housing 14. The length 15 of threaded shaft 12 (see FIG. 5) preferably exceeds the length 13 of housing 14 by at least about 10 millimeters. In one embodiment, length 15 exceeds length 13 by at least 25 millimeters. In another embodiment, length 15 exceeds length 13 by at least 50 millimeters.

In one embodiment, the threaded shaft 12 has a first natural frequency that is less than about 0.2 times as great as the first natural frequency of the housing 14. In another embodiment, the first natural frequency of the threaded shaft 12 is less than about 0.1 times as great as the first natural frequency of the housing 14.

As used herein, the term first natural frequency refers to frequency of the first normal mode of vibration; see, e.g., page 1253 of the McGraw-Hill Dictionary of Scientific and Technical Terms, Fourth Edition (McGraw-Hill Book Company, New York, N.Y., 1989. Reference also may be had to pages 5-59 to 5-70 ("Natural Frequencies of Simple Systems) of Eugene A. Avallone et al.'s "Mark's Standard Handbook for Mechanical Engineers" (McGraw-Hill Book Company, New York, N.Y., 1978). Reference also may be had to U.S. Pat. Nos. 6,125,701, 6,591,608, 6,525,456, 6,439,282, 6,170,202, 6,101,840, and the like; the entire disclosure of each of these United States patents is hereby incorporated by reference into this specification.

Figure 18:
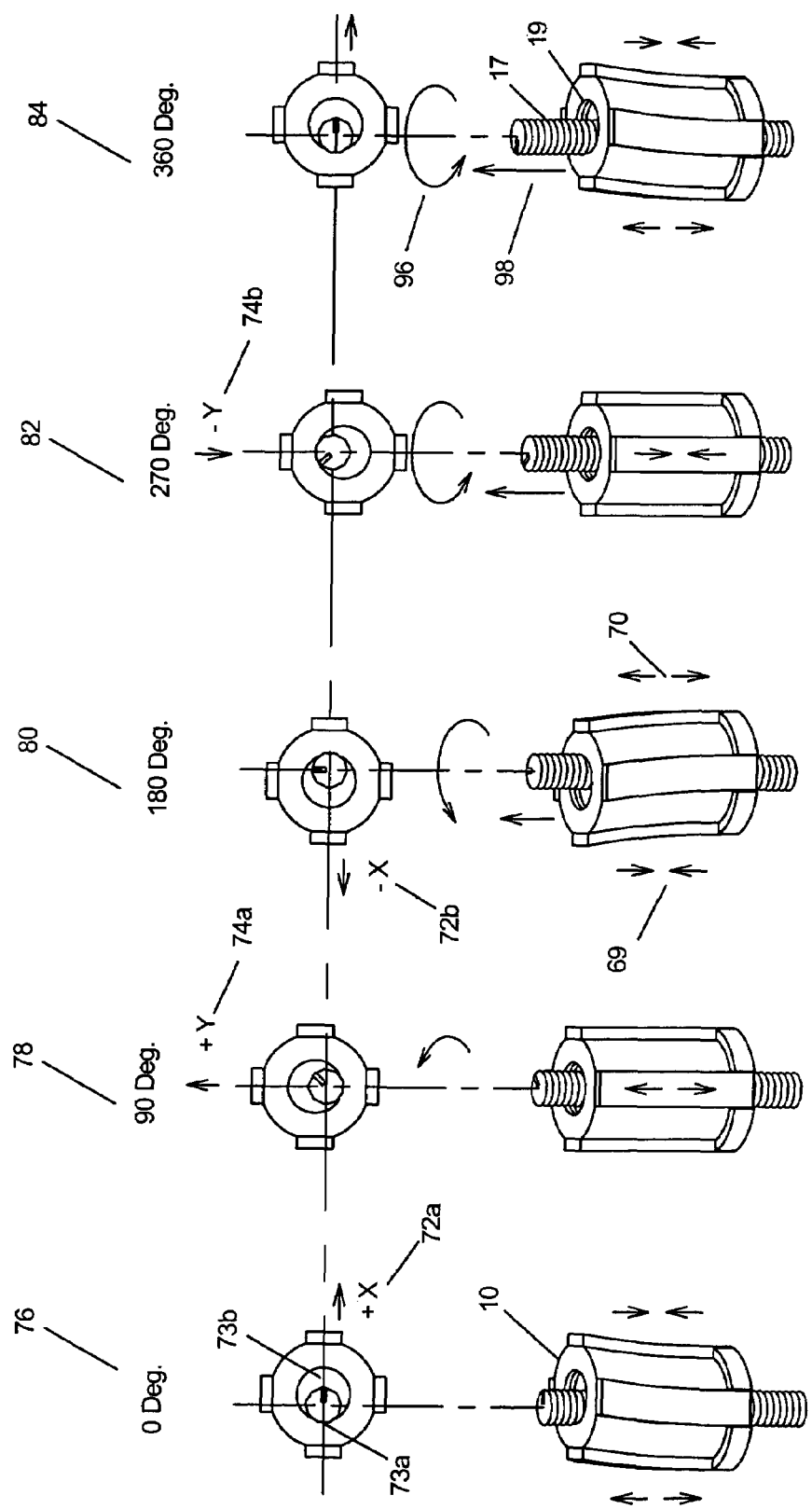
FIG. 18 is a schematic illustration of the orbital movement of threaded nut for the motor of FIG. 1 showing the rotation and translation of the threaded shaft.

In the embodiment depicted in the Figures, an orbital movement of nut 16 is created by the presence of two normal modes of vibration that are acting orthogonal to each other in planes parallel to the axis centerline (see FIG. 2), as is best illustrated in FIG. 18. These two orthogonal normal modes of vibration are provided by the interaction of the activated transducers (such as, e.g., plates 18, 20, 22, and 24) and the housing 14; and such interaction causes orbital movement of the nut 16 which, in turn, causes rotation and translation of threaded shaft 12.

In one embodiment, the first natural resonance frequency of nut 16 is preferably at least five times as great as the operating frequency of motor assembly 10. It is thus preferred that nut 16 be a substantially rigid body.

In one embodiment, the threaded shaft 12 is fabricated from metal that is substantially stainless steel. In this embodiment, the threaded shaft 12 engages with a threaded nut 16 which, is fabricated from metal that is substantially brass.

As will be apparent, it is preferred to use combinations of materials for the threaded shaft 12 and the threaded nut 16 so that abrasion and galling are minimized. Other combinations of materials that will also minimize such abrasion and galling may be used in the invention.

Referring again to FIG. 1, it will be seen that threaded shaft 12 is comprised of a multiplicity of threads 17, preferably in the form of a helical groove. In one embodiment, the threads 17 have a pitch lower than about 250 threads per inch and, preferably, less than about 200 threads per inch. In another embodiment, the threads 17 have pitch lower than about 100 threads per inch. In one aspect of this embodiment, the threads 17 have a pitch of from about 40 to about 80 threads per inch.

Figure 36:
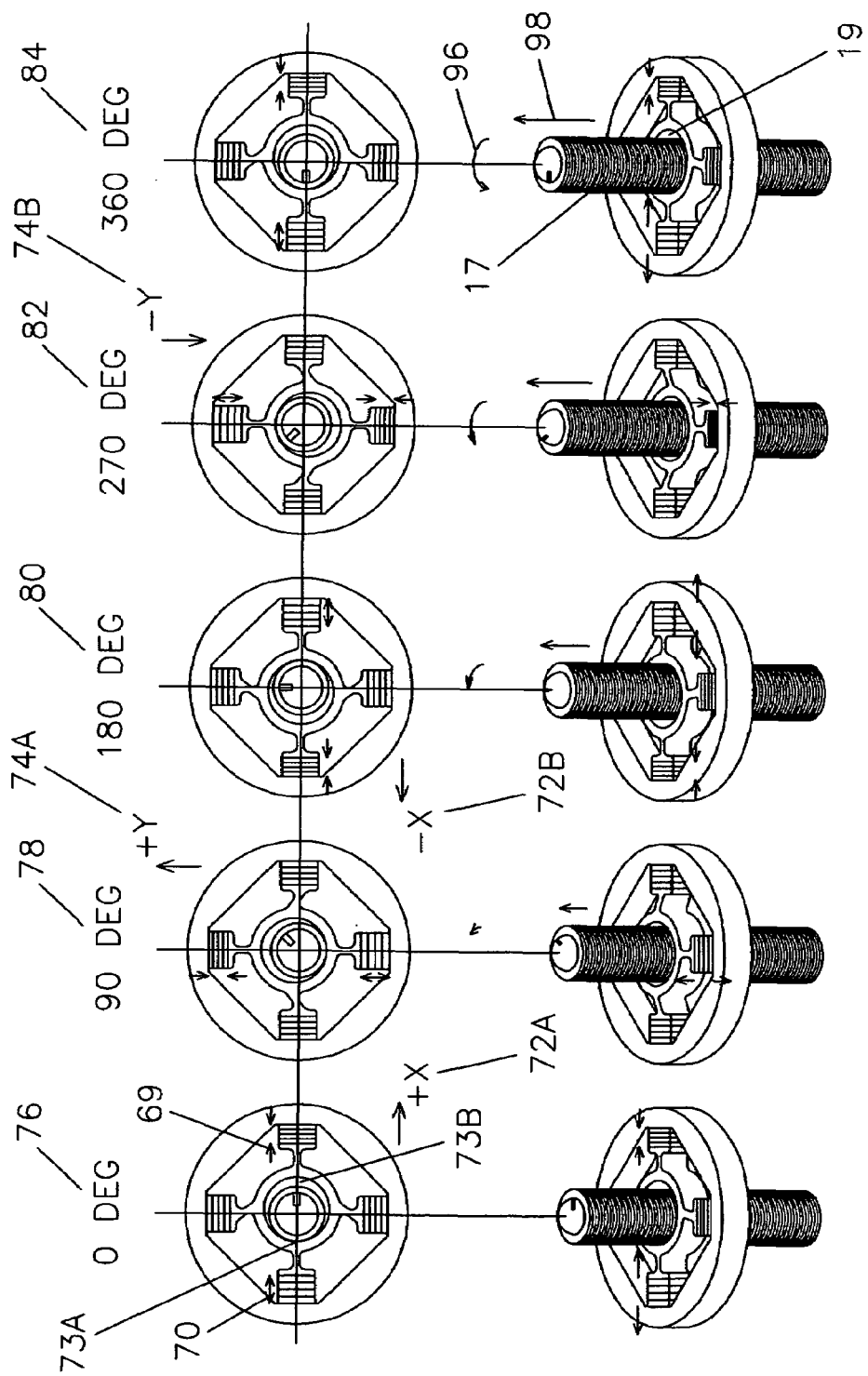

The threads 17 are preferably engaged with interior threads 19 of nut 16, as is best illustrated in FIG. 18 (also see FIG. 36). In one preferred embodiment, the pitch of interior threads 19 is substantially equal to the pitch of exterior threads 17.

Figure 5:
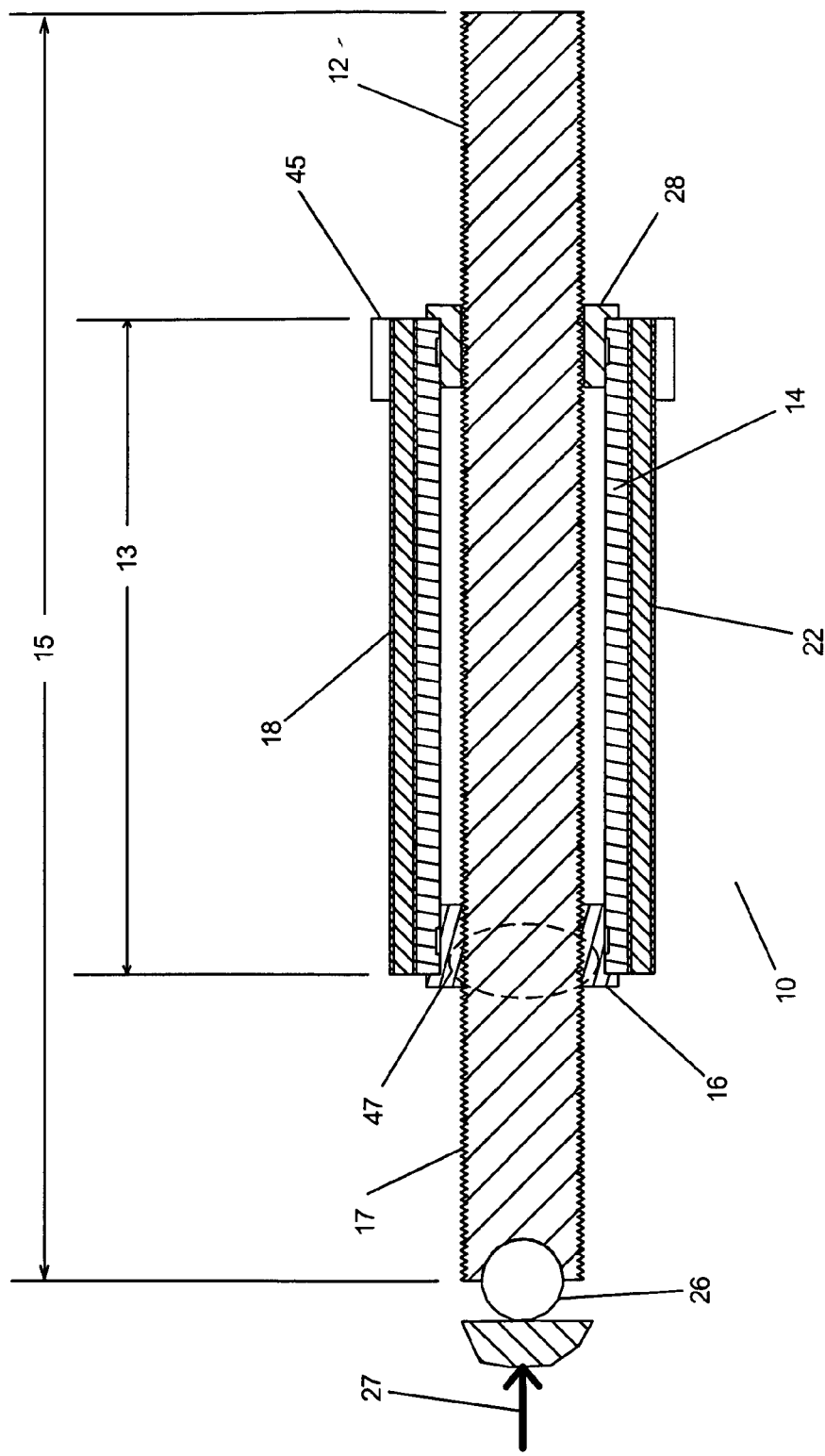
Figure 5A:
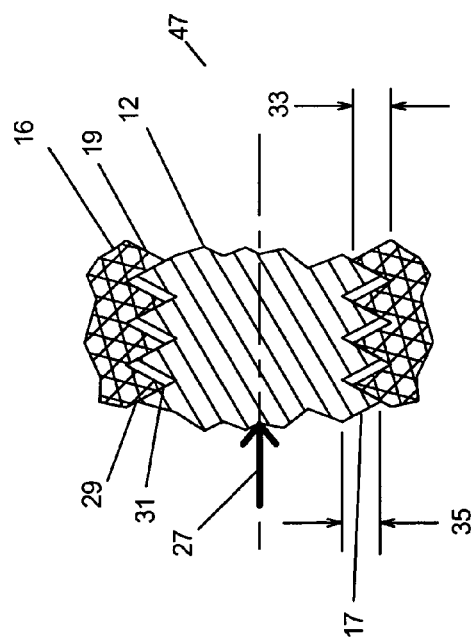
FIG. 5A shows a magnified scale view (47 on FIG. 5) of the thread engagement with external preload and the motor off, FIG. 5B show the same magnified scale view in FIG. 5A with the motor operating.
Figure 5B:
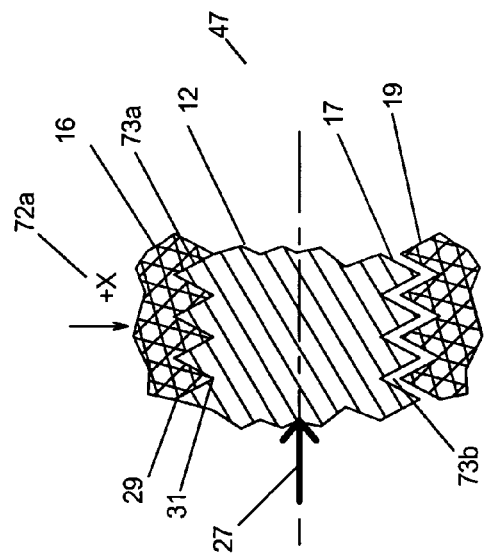
Figure 6:
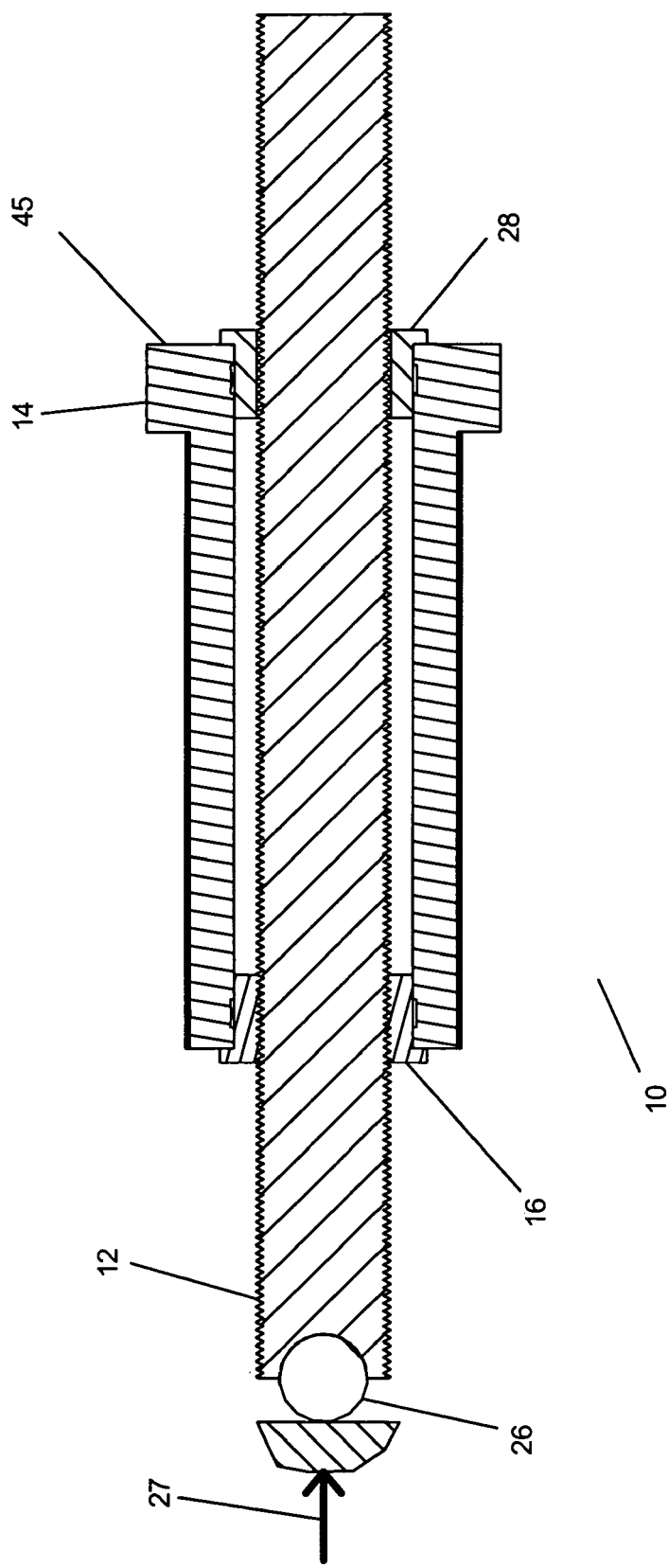
Figure 7:
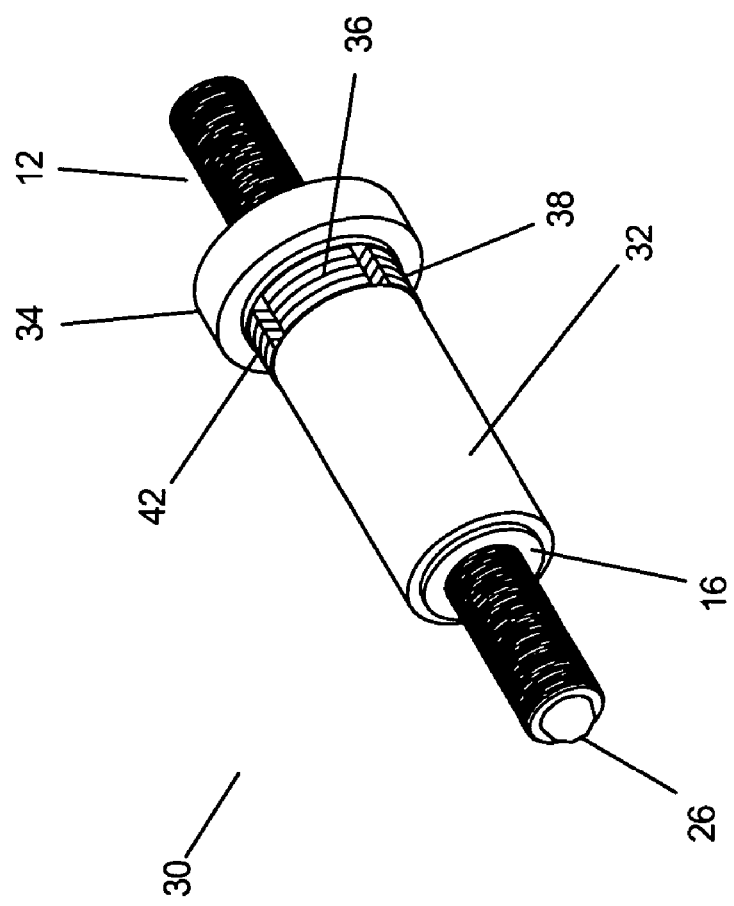
Figure 8:
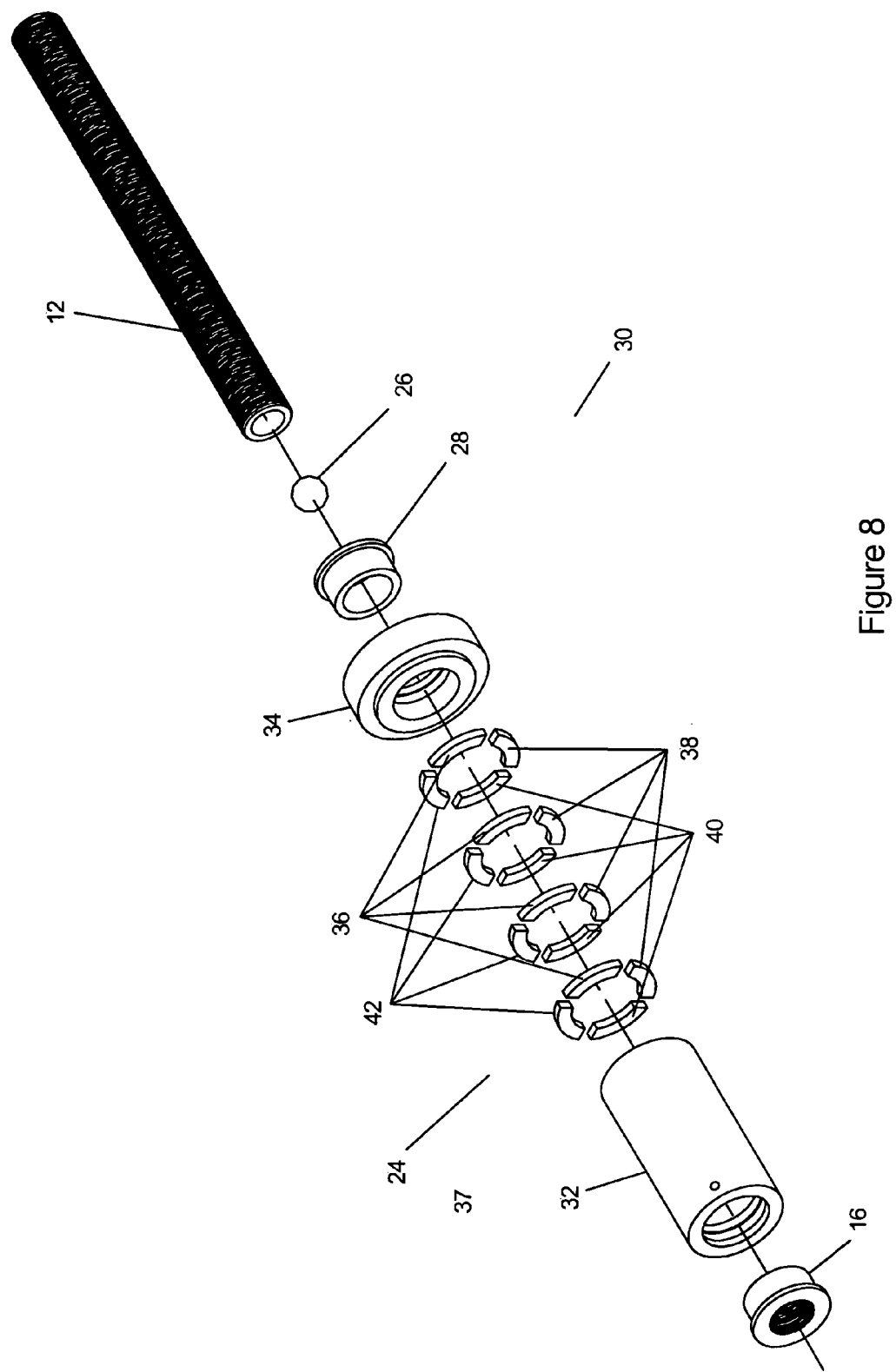
Figure 9:
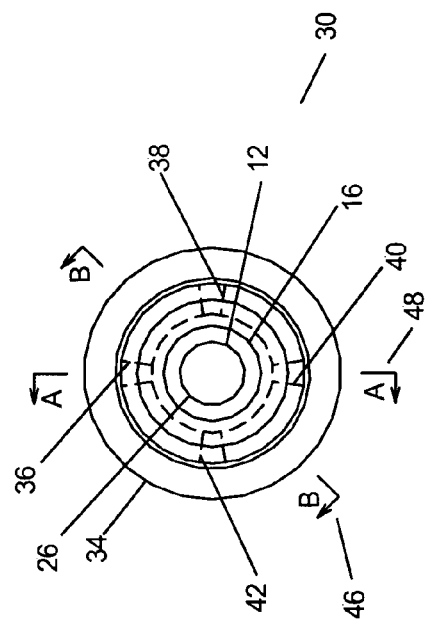
Figure 10:
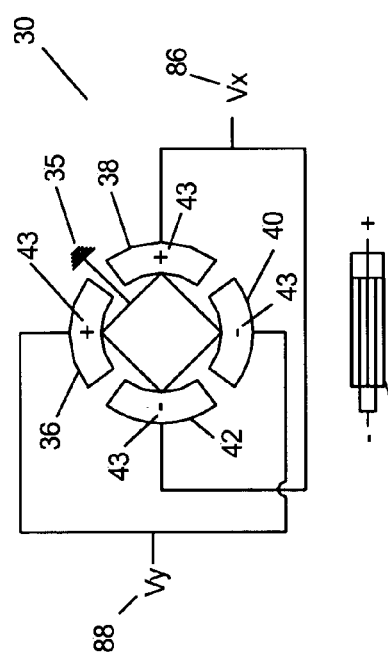
Figure 11:
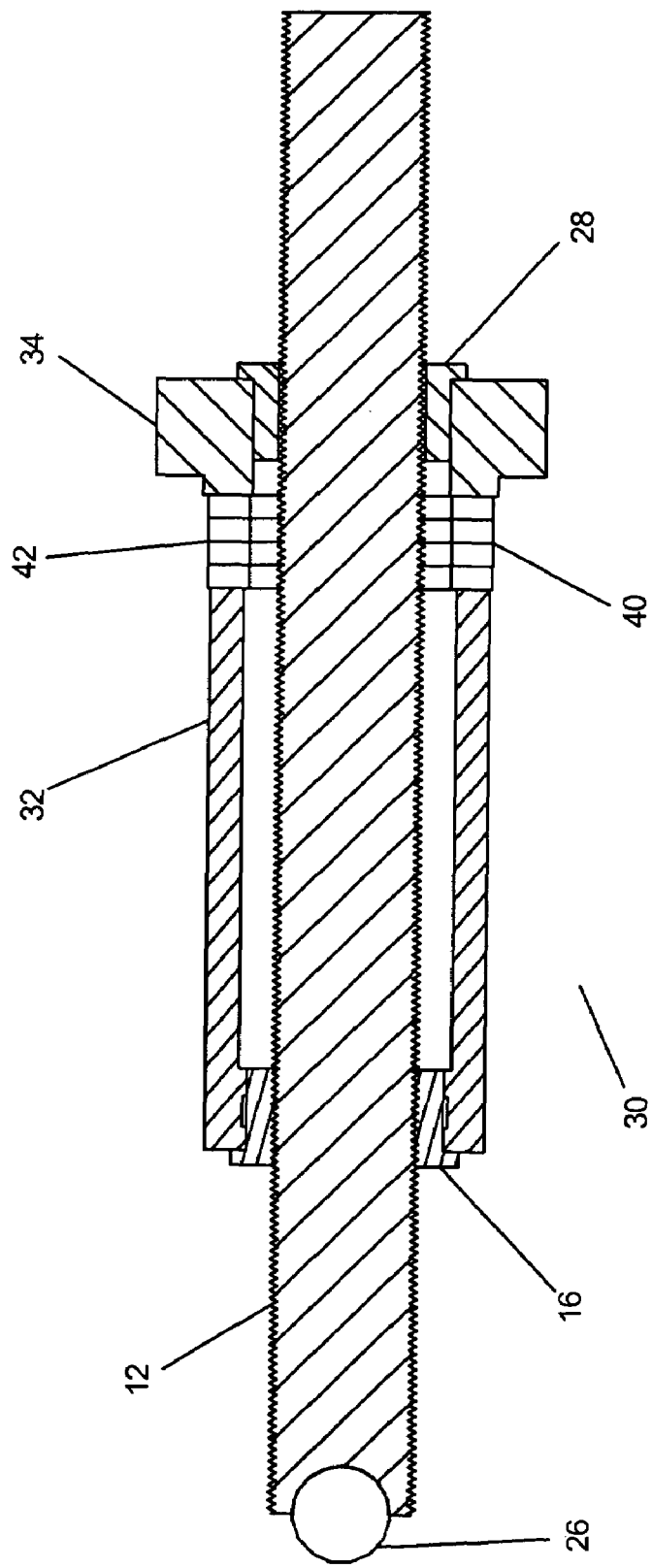
Figure 12:
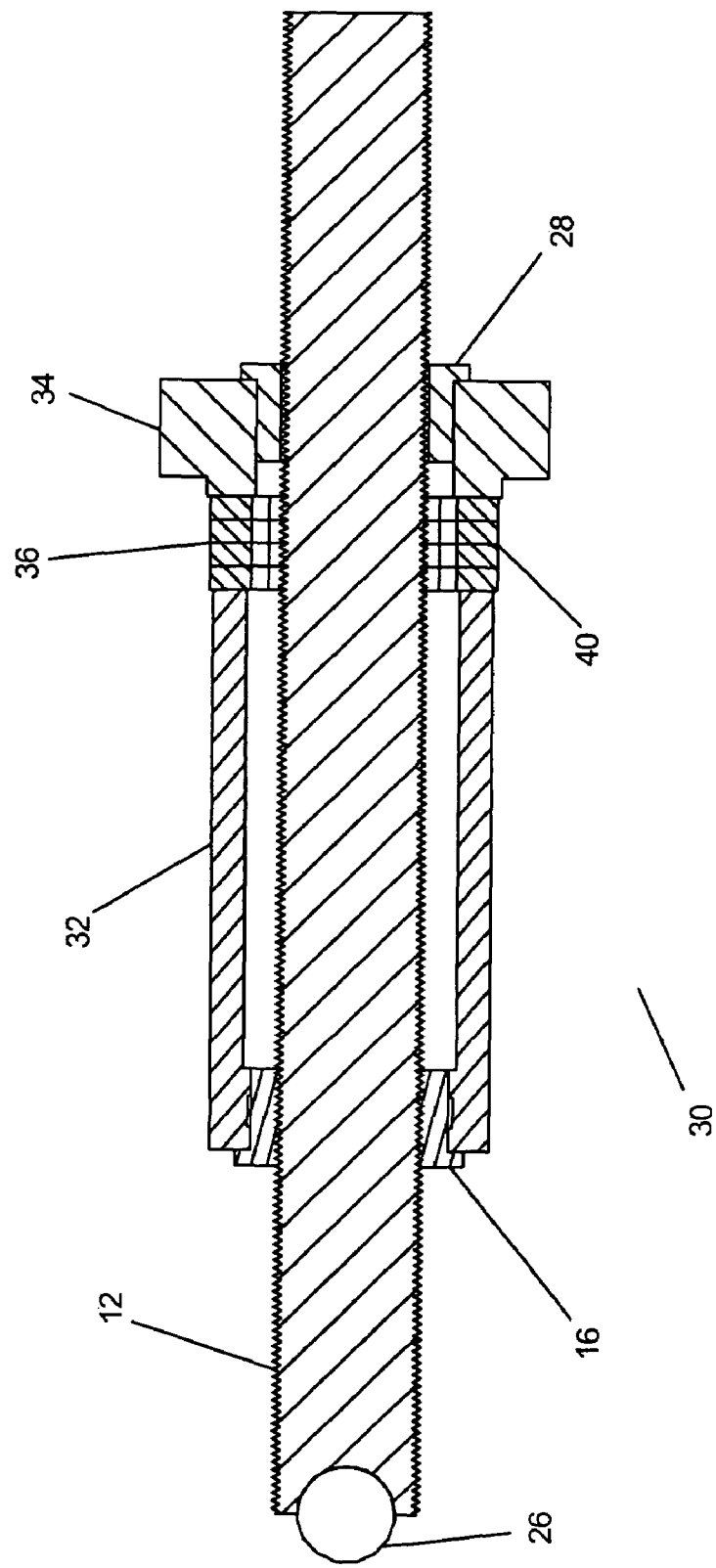
Figure 13:
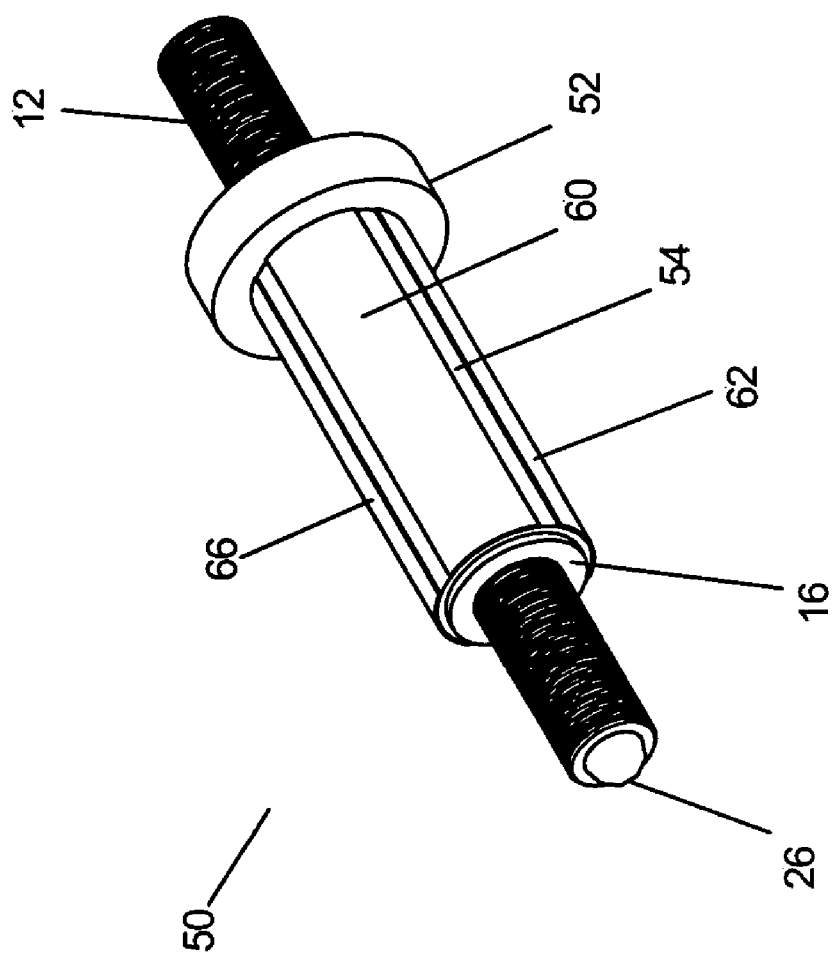
Figure 14:
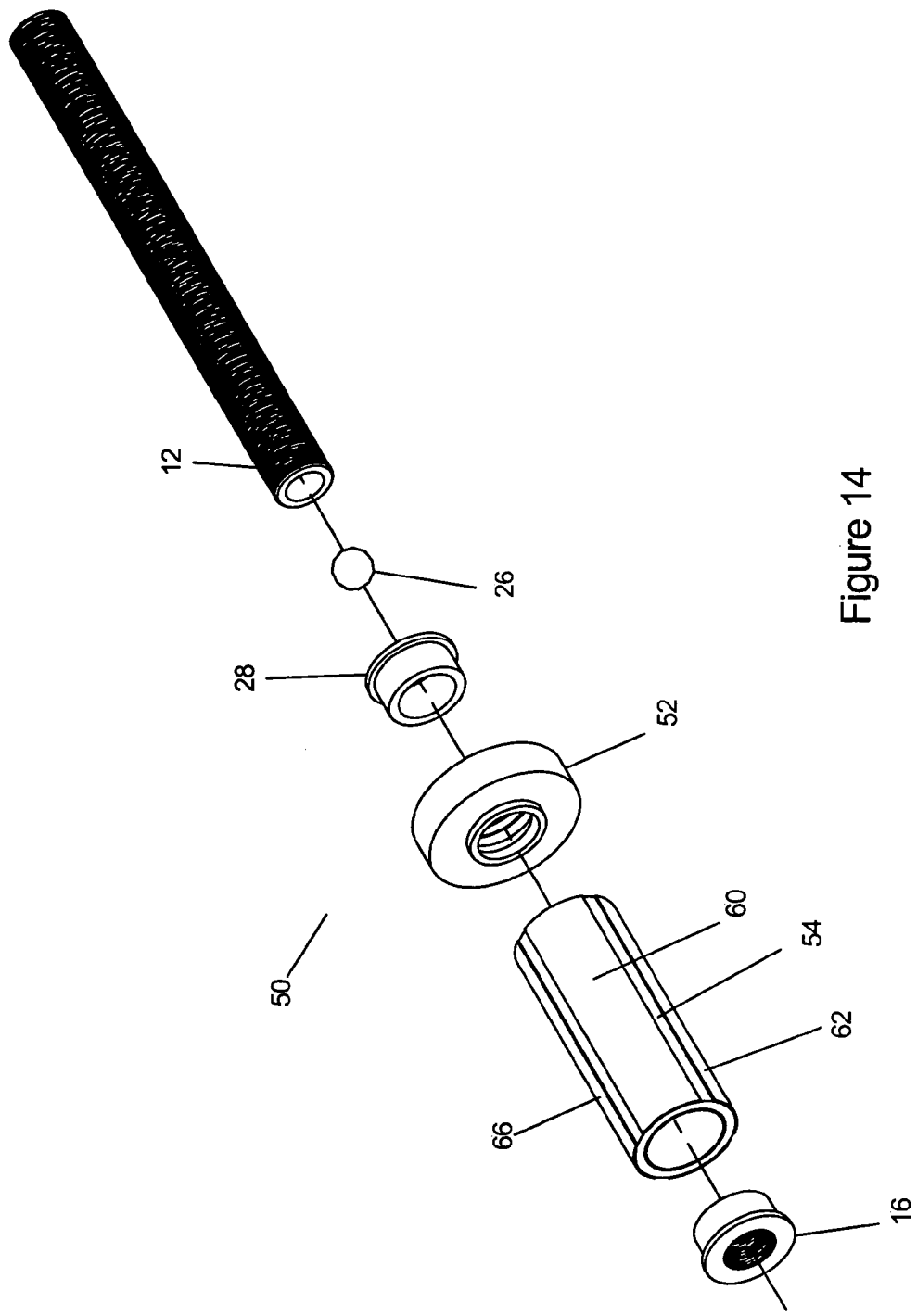
Figure 15:
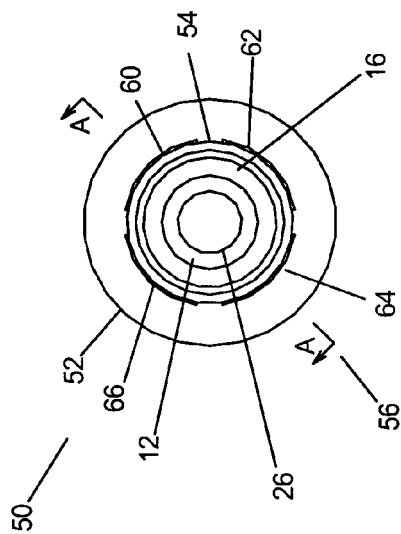
Figure 16:
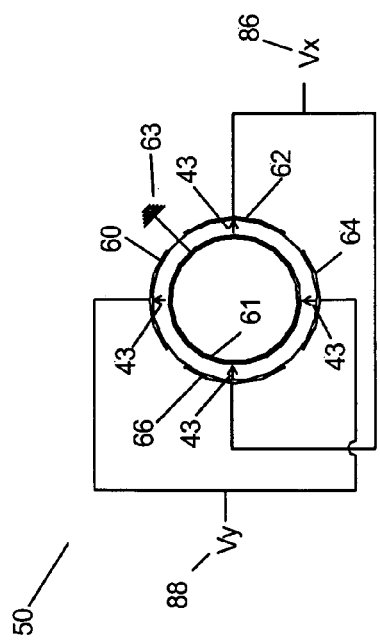
Figure 17:
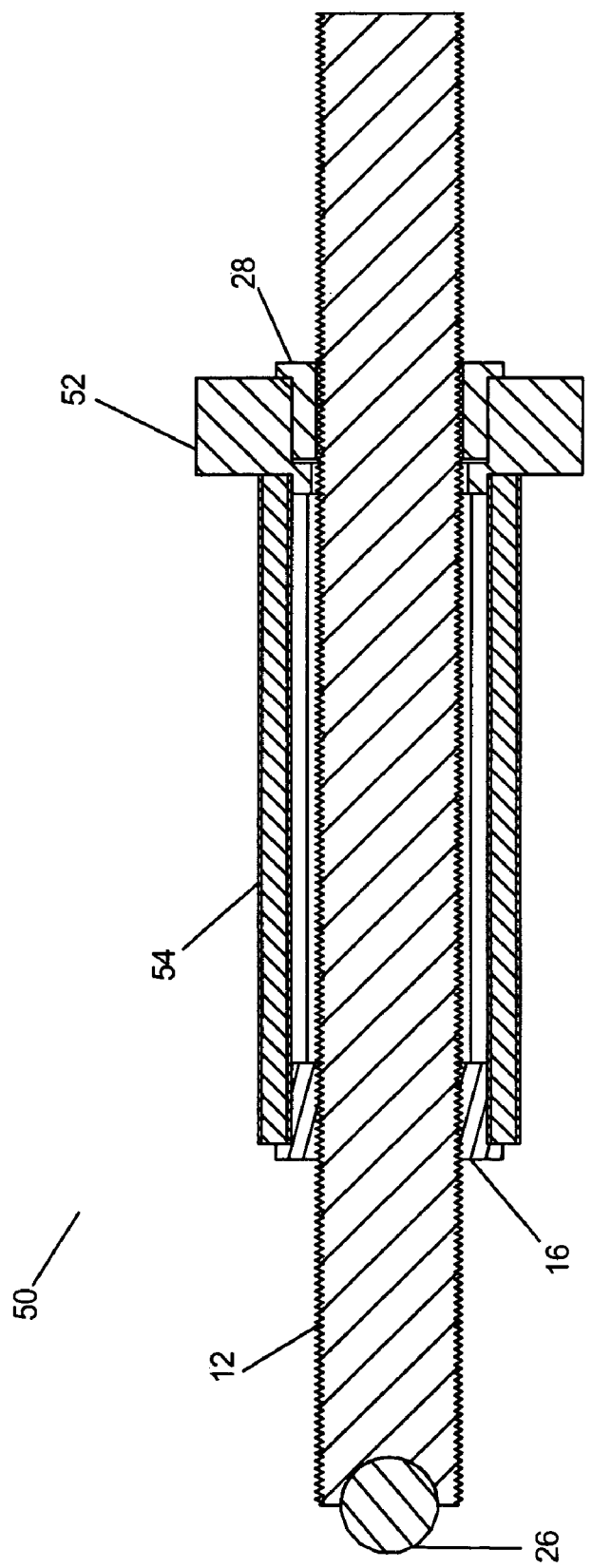

Although, for the purposes of simplicity of illustration, the threads 17 and 19 are shown totally engaged, (except for FIGS. 5A, 5B, 18 and 36) there is preferably a diametrical clearance between threads 17 and 19 of less than about 0.5 times the thread depth 33/35 of threads 17 and/or threads 19. This diametrical clearance is best illustrated in FIG. 5A. Means for determining this diametrical clearance are well known. Reference may be had, e.g., to U.S. Pat. Nos. 6,145,805, 5,211,101, 4,781,053, 4,277,948, 6,257,845, 6,142,749, and the like; the entire disclosure of each of these United States patents is hereby incorporated by reference into this specification. Reference also may be had, e.g., to pages 8-9 et seq. ("Machine Elements") of the aforementioned "Marks Standard Handbook for Mechanical Engineers."

Referring to FIG. 5A, one preferred mode of engagement between threads 17 and 19 is illustrated. As will be seen from this Figure, each of threads 17 has a tip 29, and each of threads 19 has a tip 31. Additionally, each of threads 17 and 19 has a thread depth, 33 and 35, respectively.

Referring again to FIG. 1, and in the preferred embodiment depicted therein, it will be seen that rotation of the threaded shaft 12 is produced by ultrasonic orbits of the threaded nut 16 connected to a vibrating housing 14. In the embodiment depicted, the threaded nut 16 is preferably connected to the housing 14. This is best illustrated in FIG. 2.

Figure 2:
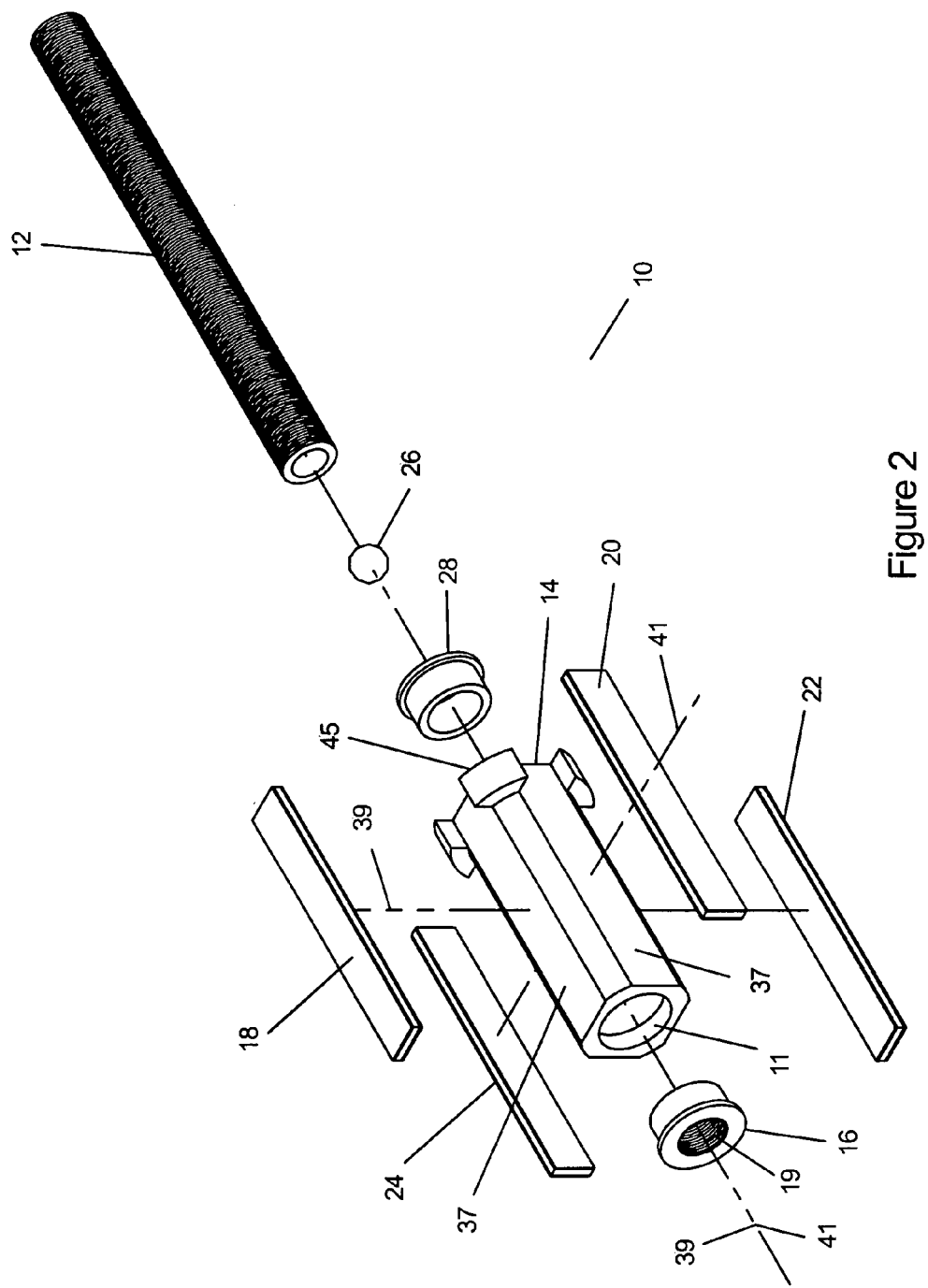

Referring to FIG. 2, and in the preferred embodiment depicted therein, it will be seen that nut 16 is disposed within orifice 11. The nut 16 is secured within orifice 11 by conventional means such as, e.g., a press fit, and/or adhesive means, etc.

In the preferred embodiment depicted in FIGS. 1 and 2, nut 16 is a cylindrical nut. In another embodiment, not shown, nut 16 is a polygonal nut that may have a square shape, a hexagonal shape, an octagonal shape, etc.

Referring again to FIGS. 1 and 2, and in the preferred embodiment depicted therein, it will be seen that a multiplicity of ceramic plates 18 et seq. are attached to the outside surface 37 of the housing 14.

It is preferred that the ceramic plates 18 et seq. change their respective lengths upon being subjected to a electrical voltage and, in particular, to a change in electrical voltage. As used therein, and as is described elsewhere in this specification, these ceramic plates may be described as "active ceramic plates." In one embodiment, the active ceramic plates 18 et seq. are selected from the group consisting of piezoelectric plates, electrostrictive plates, and mixtures thereof. For the sake of simplicity of discussion, the embodiments of at least FIGS. 1 and 2 will be described with reference to piezoelectric plates.

In the embodiment depicted in FIG. 2, four piezoelectric plates 18, 20, 22, and 24 are bonded to the outside surface 37 of the housing and generate the nut 16 orbital vibrations when excited by alternating electrical drive signals on electrodes 21 and 23 on each piezoelectric plate (see FIG. 4).

In one embodiment, only two such piezoelectric plates are used, plates 18 and 20. In another embodiment, eight or more piezoelectric plates are used. Regardless of how many such piezoelectric plates are used, a sufficient number of such plates are used to excite motion in orthogonal planes 39 and 41 (see FIG. 2).

For the sake of simplicity of representation, four piezoelectric plates 18, 20, 22, and 24 will be discussed. These plates are preferably bonded to the corresponding exterior surfaces 37 of housing 14 so that the plates are completely contiguous with such exterior surfaces 37.

The piezoelectric plates 18 et seq. are connected to a source of electrical voltage by electrodes 21 and 23, as is best shown in FIG. 4. As will be apparent, and for the sake of simplicity of representation, the connection of electrodes 21 and 23 is shown only with reference to piezoelectric plate 20, it being understood that comparable connections are made with respect to the other piezoelectric plates.

Referring to FIG. 4, and to the preferred embodiment depicted therein, it will be seen that all four inside electrodes 23 are connected to ground 25. In this embodiment, the piezoelectric material is a commonly available "hard" composition with low dielectric losses and high depoling voltage. Thus, for example, one may use a piezoelectric material sold as "PZT-4" by the Morgan Matroc company of Bedsford, Ohio. This preferred material typically has several important properties.

Thus, the preferred material preferably has a dielectric loss factor of less than about 1 percent at a frequency greater than about 20,000 Hertz and, preferably, less than about 0.5 percent. In one embodiment, the dielectric loss factor is about 0.4 percent at a frequency greater than about 20,000 Hertz.

Thus, the preferred material has a d33 piezoelectric charge coefficient of at least about 250 picoCoulomb/Newton's and, preferably, at least about 270 picoCoulomb/Newton's. In one embodiment, the preferred material has a d33 piezoelectric charge coefficient of about 285 picoCoulomb/Newton's.

Thus, the preferred material has a d31 piezoelectric charge coefficient of at least about—90 picoCoulomb/Newton's and, more preferably, at least about—105 picoCoulomb/Newton's. In one embodiment, the d31 piezoelectric charge coefficient is about—115 picoCoulomb/Newton's.

In one embodiment, the preferred material is a single crystal material with a d33 piezoelectric charge coefficient of at least about 2500 picoCoulomb/Newton's, and a d31 piezoelectric charge coefficient of at least about 900 picoCoulomb/Newton's For a discussion of some suitable materials, and by way of illustration and not limitation, reference may be had, e.g., to U.S. Pat. Nos. 3,736,532 and 3,582,540. The entire disclosure of each of these United States patents is hereby incorporated by reference into this specification.

By way of further illustration, and as is known to those skilled in the art, low dielectric-loss piezoelectric materials are known to those skilled in the art. Reference may be had, e.g., to U.S. Pat. No. 5,792,379 (low-loss PZT ceramic composition); the entire disclosure of this United States patent is hereby incorporated by reference into this specification.

In one embodiment, the piezoelectric material is a single crystal piezoelectric material. These materials are known in the art. Reference may be had, e.g., to United States Pat. Nos. 5,446,330, 5,739,624, 5,814,917, 5,763,983 (single crystal piezoelectric transformer), 5,739,626, 5,127,982, and the like. The entire disclosure of each of these United States patents is hereby incorporated by reference into this specification.

Referring again to FIG. 4, and in the preferred embodiment depicted therein, the axial length of the piezoelectric plates 18, 20, 22, and 24 changes in proportion the applied voltage (Vx/86 and Vy/88) and the $d_{31}$ piezoelectric charge coefficient.

As will be apparent, piezoelectric plates 18,22 and 20,24 work together in pairs, respectively, to bend the housing 14 (see, e.g., FIGS. 1 and 2) and excite the orbital resonance. Alternating electric drive signals 86 and 88 are preferably applied to plates 20,24 and 18,22, respectively, with poling directions 43. As is well known to those skilled in the art, poling directions 43 are the directions in which the dipoles in the piezoelectric material are aligned during manufacture. Reference may be had, e.g., to U.S. Pat. Nos. 5,605,659 (method for poling a ceramic piezoelectric plate), 5,663,606 (apparatus for poling a piezoelectric actuator), 5,045,747 (apparatus for poling a piezoelectric ceramic), and the like. The disclosure of each of these United States patents is hereby incorporated by reference into this specification.

For each plate pair 18,22 and 20,24 the electric field is positive with respect to the poling direction 43 on one plate and negative with respect to the poling direction 43 on the opposite plate. Drive signal Vx 86 is preferably applied to plates 20,24 and produces simultaneous expansion on one plate and contraction on the opposite plate and thus bends the housing 14 in the plane 39 (see FIG. 2), and in the X direction 72a/72b (see FIG. 18). In a similar manner the drive signal Vy 88 is applied to plates 18,22 and bends the housing 14 in the plane 41 (see FIG. 2), and in the Y direction 74a/74b (see FIG. 18).

The housing end 45 opposite the threaded nut 16 preferably supports a guide bushing 28 with a small clearance between the bushing inside diameter and the outside diameter of the threaded shaft 12 (see FIG. 2). The threaded shaft 12 supports a resilient axial force 27 (see FIGS. 5 and 6) that is applied via the spherical ball tip 26 using a hard flat surface that produces low friction.

It is preferred that, during the operation of the motor 10, the axial force 27 that is preferably transmitted through ball 26 be from about 0.1 to about 100 Newton's. As will be apparent, the axial force 27 preferably is of similar magnitude to the output driving force. The spherical ball 26 (see FIG. 2) is one means of coupling threaded shaft 12 to its load 27 (see FIG. 5) with low frictional torque. As will be apparent to those skilled in the art, one may use other means for coupling motion from a rotating threaded shaft to a moving load. Thus, e.g., one may use a rolling element bearing, one may use an arcuate load contiguous with a flat surface on threaded shaft 12, etc. Reference may be had, e.g., to U.S. Pat. Nos. 5,769,554 (kinematic coupling method), 6,325,351 (highly damped kinematic coupling for precision instruments), etc.; the entire disclosure of each of these United States patents is hereby incorporated by reference into this specification.

Figure 21:
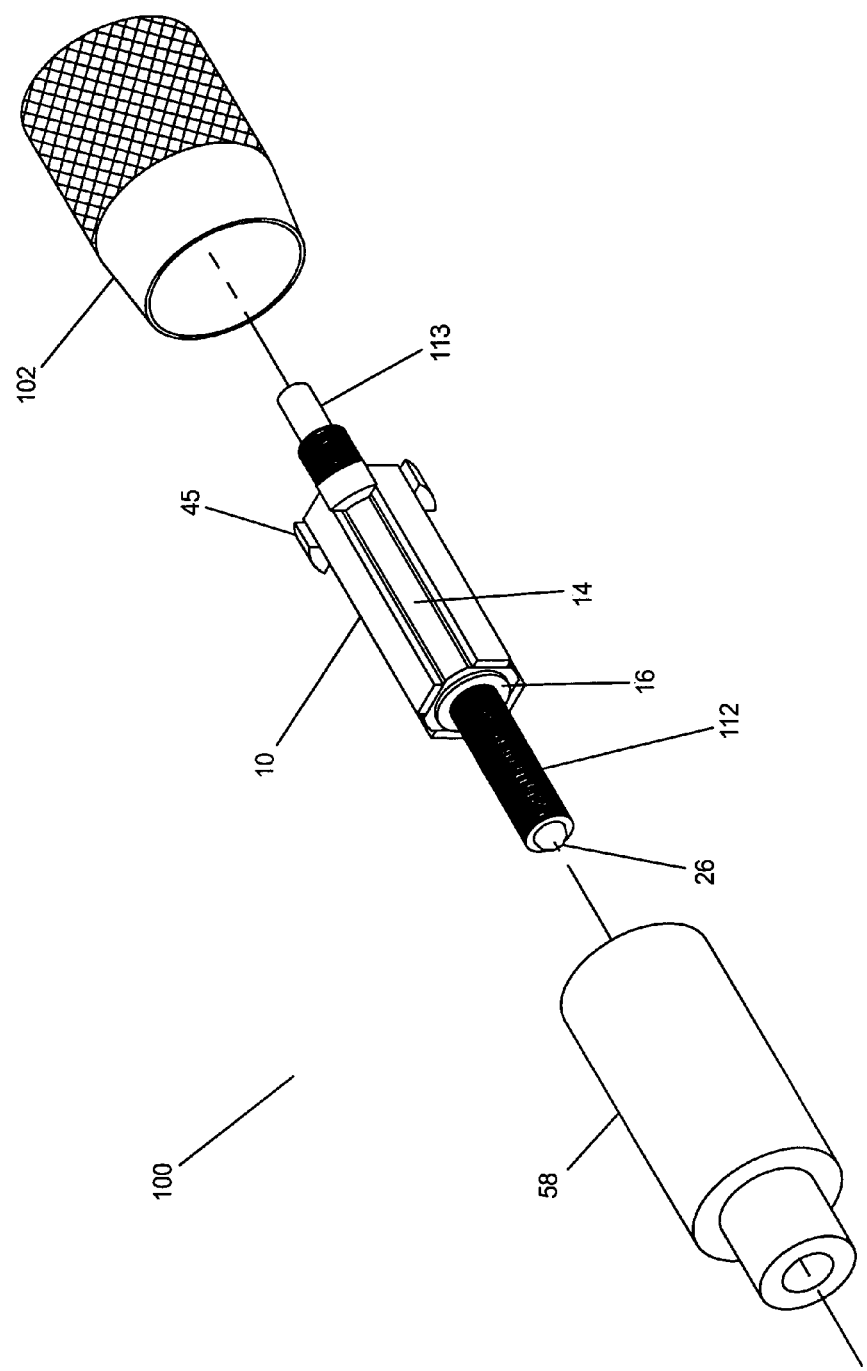

Referring to FIGS. 1 and 2, the end 45 of the housing 14 opposite the threaded nut 16 incorporates flanges that are the connection point for a stationary cover 58 (FIG. 21). The thread pitch on the shaft 12 and on the nut 16 converts the orbital tangential force and movement to axial force and movement. The pitch may be selected to optimize the force magnification, speed reduction, resolution enhancement and off-power holding force.

Referring to FIGS. 7 through 12, and in the preferred embodiment depicted therein, the ultrasonic linear motor 30 preferably uses four piezoelectric stacks 36, 40 and 42 (also see FIGS. 7 and 8) to generate ultrasonic vibrations. A threaded shaft 12 with a spherical ball tip 26 rotates and produces axial force and motion. The rotation is produced by an ultrasonic orbits of the threaded nut 16 connected to a vibrating cylinder 32. Four piezoelectric stacks 36, 38, 40, and 42 are bonded to the end of the cylinder opposite the threaded nut and bonded to the base ring 34. The four stacks 36 et seq. are constructed using well-known assembly and electrical interconnection methods 44 with the inside stack leads preferably being connected together to a common ground 35. The axial length of the stacks 36 et seq. changes in proportion to the applied voltage and the $d_{33}$ piezoelectric charge coefficient. The piezoelectric material is a commonly available "hard" composition with low dielectric losses and high depoling voltage. Alternating electrical drive signals 86 and 88 are connected to the outside leads of each piezoelectric stack 44 and excite orbital vibrations of the nut. Piezoelectric stacks 36 and 40 and 38 and 42 work together in pairs, respectively, to rotate the tube and excite the orbital resonance. Alternating electric drive signals Vx 86 and Vy 88 are applied to stacks 38,42 and 36,40, respectively, with poling directions 43. For each stack pair 38,42 and 36,40, the electric field is positive with respect to the poling direction 43 on one stack and negative with respect to the poling direction on the opposite stack. Drive signal Vx 86 is applied to stacks 38,42 and produces simultaneous expansion on one stack and contraction on the opposite stack; and thus it rotates the tube in the X direction 72a/72b (see FIG. 18). In a similar manner, the drive signal Vy 88 is applied to stacks 36,40 and moves the end of the tube in the Y direction 74a/74b (see FIG. 18). The base ring 34 opposite the threaded nut 16 supports a guide bushing 28 with a small clearance between the bushing inside diameter and the outside diameter of the threaded shaft. The threaded shaft 12 supports a compliant axial force 27 that is applied via the spherical ball tip 26 using a hard flat surface that produces low friction. The base ring 34 is the connection point for a stationary cover 58 (FIG. 21). The thread pitch on the shaft 12 and nut 16 converts the orbital tangential force and movement to axial force and movement. The pitch may be selected to optimize the force magnification, speed reduction, resolution enhancement and off-power holding force.

Referring to FIGS. 13 through 17, the ultrasonic linear motor 50 uses a piezoelectric tube 54 with quadrant electrodes to generate ultrasonic vibrations. A threaded shaft 12 with a spherical ball tip 26 rotates and produces axial force and motion. The rotation is produced by ultrasonic orbits of the threaded nut 16 connected to a vibrating piezoelectric tube 54. The inside diameter of the tube is a continuous electrode 61, which is grounded 63, and the outside diameter of the tube is divided into four separate electrodes 60, 62, 64, and 66. The piezoelectric material is a commonly available "hard" composition with low dielectric losses and high depoling voltage. The axial length of the portion of the piezoelectric tube beneath each electrode 60, 62, 64, and 66 changes in proportion the applied voltage and the $d_{31}$ piezoelectric charge coefficient. Electrode sections 60,64 and 62,66 work together in pairs respectively to bend the tube 54 and excite the orbital resonance. Alternating electric drive signals 86 and 88 are applied to plates 60,64 and 62,66, respectively, with poling directions 43. For each electrode pair 60,64 and 62,66, the electric field is positive with respect to the poling direction on one electrode and negative with respect to the poling direction on the opposite electrode. Drive signal Vx 86 is applied to electrodes 60,64 and produces simultaneous expansion under one electrode and contraction under the opposite electrode; and thus it bends the tube in the X direction 72a/72b (see FIG. 18). In a similar manner the drive signal Vy 88 is applied to plates 62,66 and bends the tube in the Y direction 74a/74b (see FIG. 18).

The tube end opposite the threaded nut 16 is bonded to a base flange 52 and holds a guide bushing 28 with a small clearance between the bushing inside diameter and the outside diameter of the threaded shaft. The threaded shaft 12 supports a compliant axial force 27 that is applied via the spherical ball tip 26 using a hard flat surface that produces low friction. The base flange is the connection point for a stationary cover 58 (FIG. 21). The thread pitch on the shaft 12 and nut 16 converts the orbital tangential force and movement to axial force and movement. The pitch may be selected to optimize the force magnification, speed reduction, resolution enhancement and off-power holding force.

Figure 19:
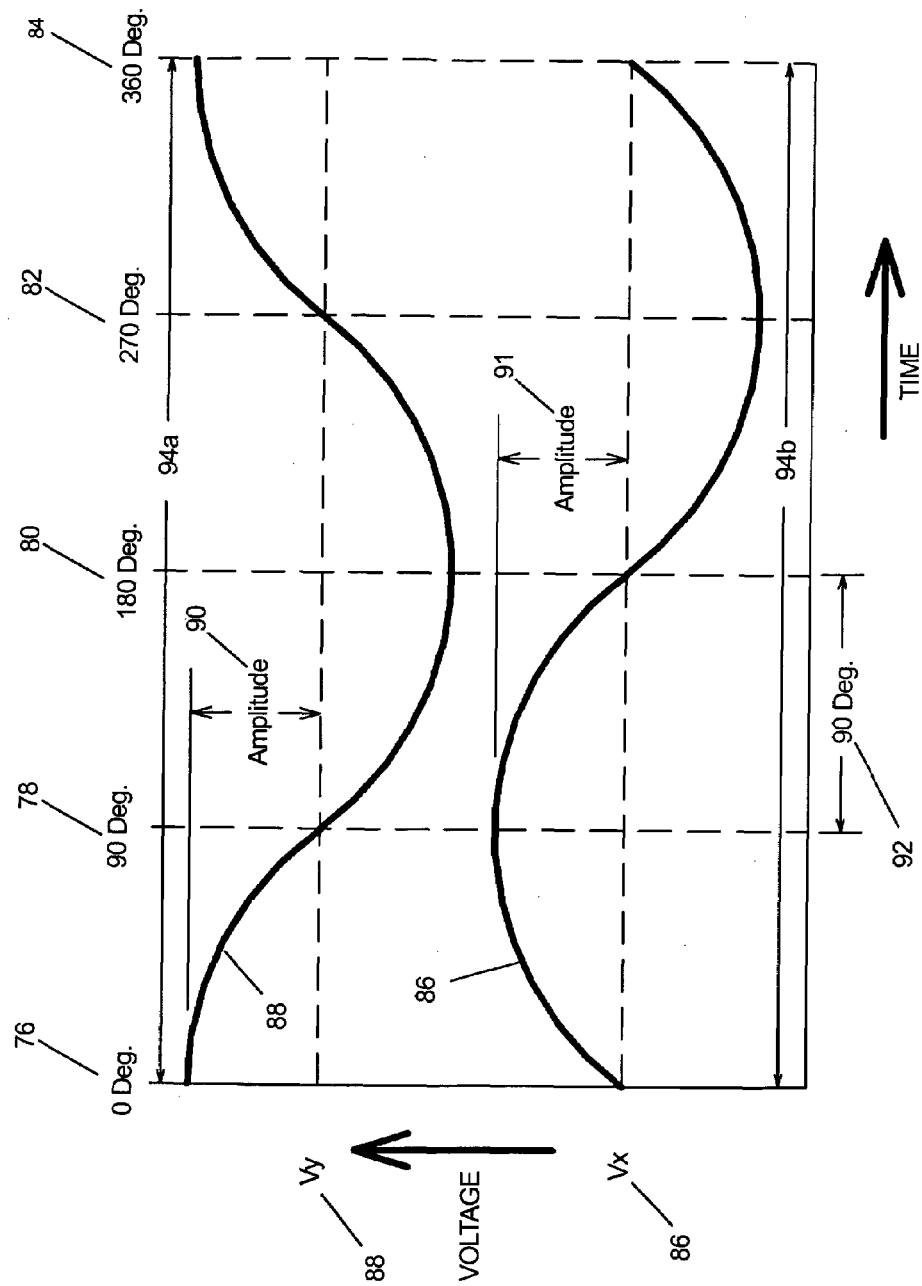
FIG. 19 is a schematic illustration of the electrical drive signals required to create the movements shown in FIG. 18.
Figure 20:
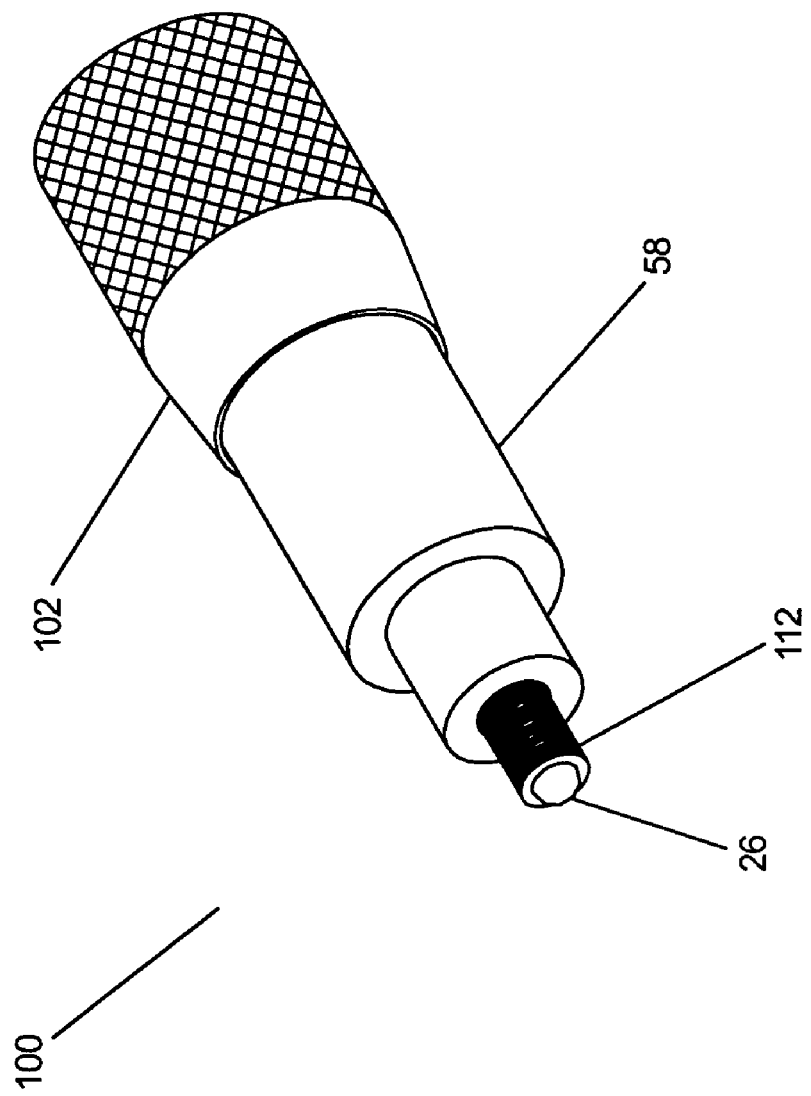

Referring to FIGS. 18 and 19, the motor 10 (see FIG. 1) operation and corresponding drive signals 86 and 88 used to effect such operation are shown (see also FIG. 36). The piezoelectric plate pairs work together, with one expanding 70 while the other simultaneously contracts 69, to bend the housing. The alternating drive signals Vx 86 and Vy 88 are preferable sinusoidal with equal amplitude 90/91 and a ninety degree phase shift 92 to produce a circular orbit. A positive phase shift 92 produces a positive nut 16 orbit direction and a positive shaft 12 rotation 96/translation 98, while a negative phase shift 92 produces a negative orbit direction and a negative shaft rotation/translation. A single orbital cycle of the motor, for one direction of rotation, and the corresponding drive signal amplitudes 90 and 91, are shown sequentially in ninety degree increments 76, 78, 80, 82 and 84. The cylindrical bending and orbital movement is shown in the X 72a/72b and Y 74a/74b directions. The nut contacts the side of the threaded shaft at one location 73a with a clearance 73b on the opposite side (see FIG. 5B), whereby the contact imparts tangential force and movement that causes the shaft 12 to rotate 96 and translate 98 a small amount for each orbital cycle. The amount of rotation and translation per cycle depends on many factors, including orbit amplitude, the magnitude of the force 27 acting on the shaft, and the coefficient of friction and surface finish of the threads. If a zero-slip condition is achieved between the contact 73a of the nut and shaft, the movement per cycle is nominally proportional to the diametrical clearance between the threads. In general, as drive amplitudes 90 and 91 increase, the orbit diameter increases, the normal contact force between the shaft 12 and nut 16 increases, slippage decreases, speed increases, and torque/force increases.

The ultrasonic frequency is the inverse of the period (see periods 94a and 94b of FIG. 19); and such ultrasonic frequency is preferably the same for both signals and matches the first bending resonant frequency of the housing 14.

Referring to FIGS. 20 through 25 the motor assembly 100 is integrates motor 10 with cover 58 and knurled knob 102. A threaded shaft 112 is disposed within the motor 10. As is best shown in FIG. 21, the threaded shaft 112 is similar to threaded shaft 12 (see FIG. 1) but differs therefrom in having a smooth spindle 113 integrally attached thereto. The spindle 113 is adapted to be attached to knurled knob 102. Cover 58 is attached to motor 10 at flange 45. Knurled knob 102 rotates and translates with shaft 112 without contacting cover 58.

Figure 22:
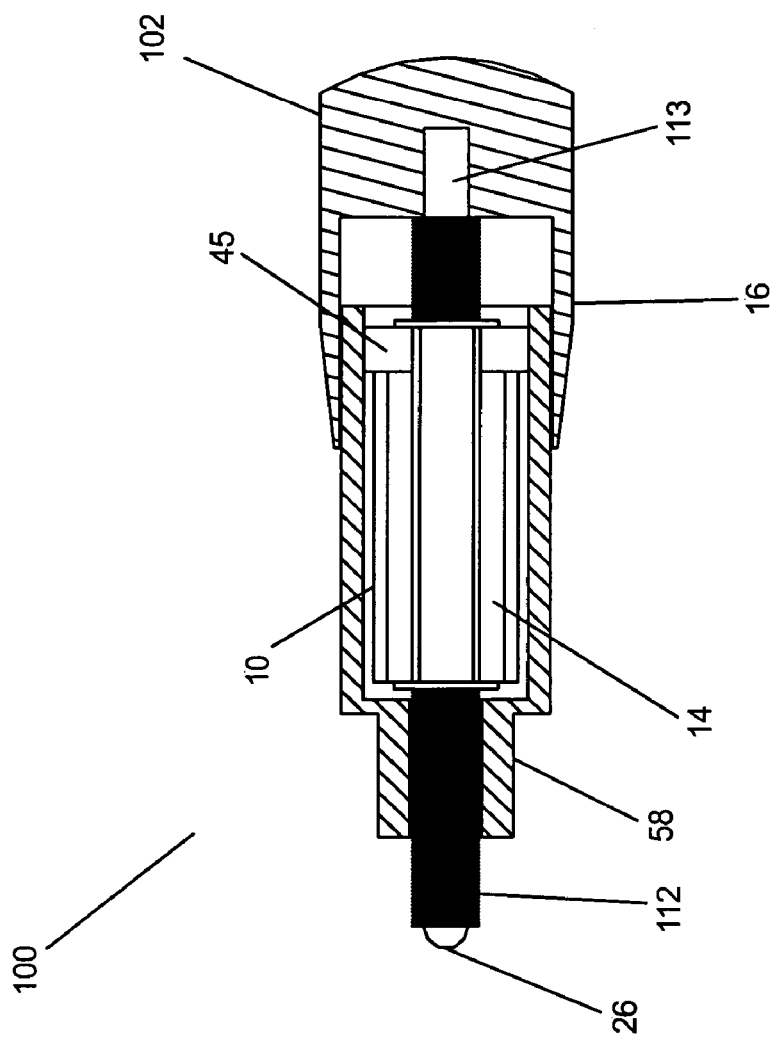

FIG. 21 is an exploded view of motor assembly 100. FIG. 22 is a sectional view of motor assembly 100.

Figure 23A:
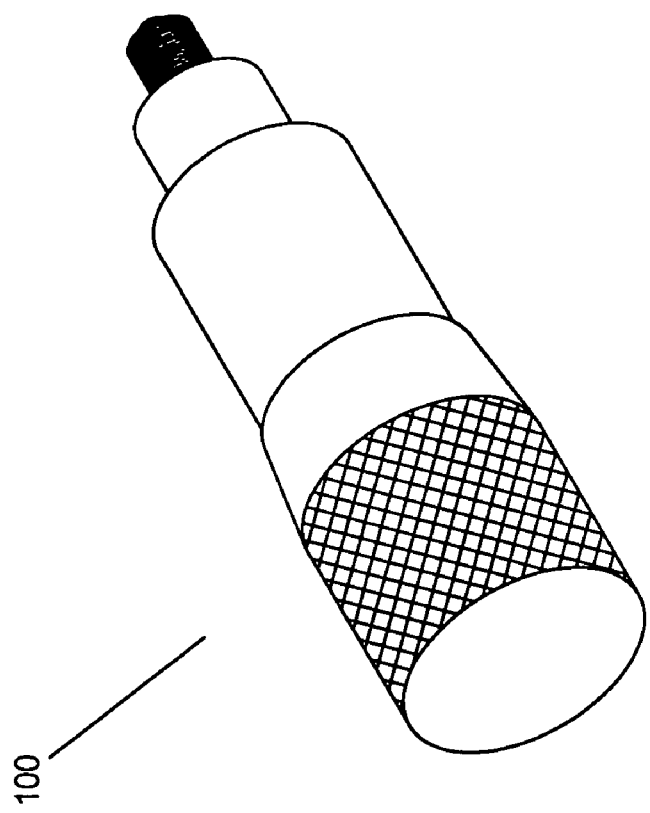
FIG. 23A is a perspective view of the motor assemble with a reverse view from FIG. 20.
Figure 23B:
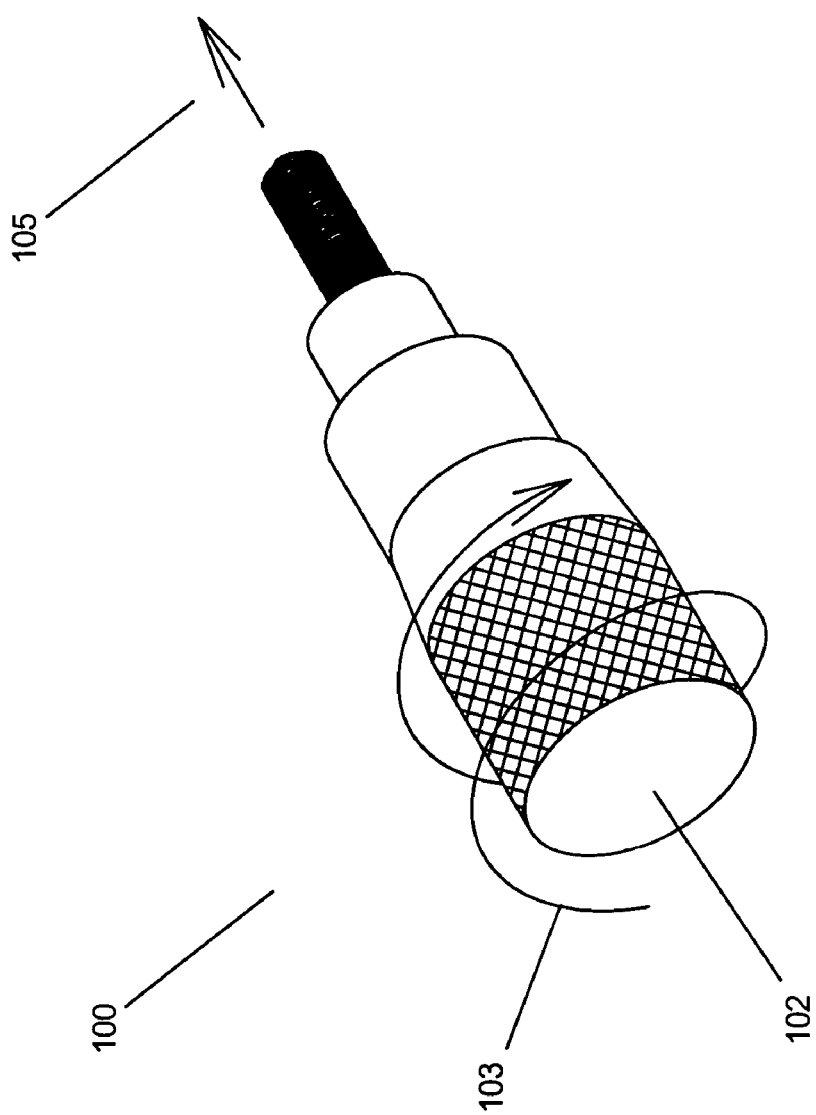
FIG. 23B is a perspective view that illustrates of how the motor assembly rotates and translates in the forward direction.
Figure 23C:
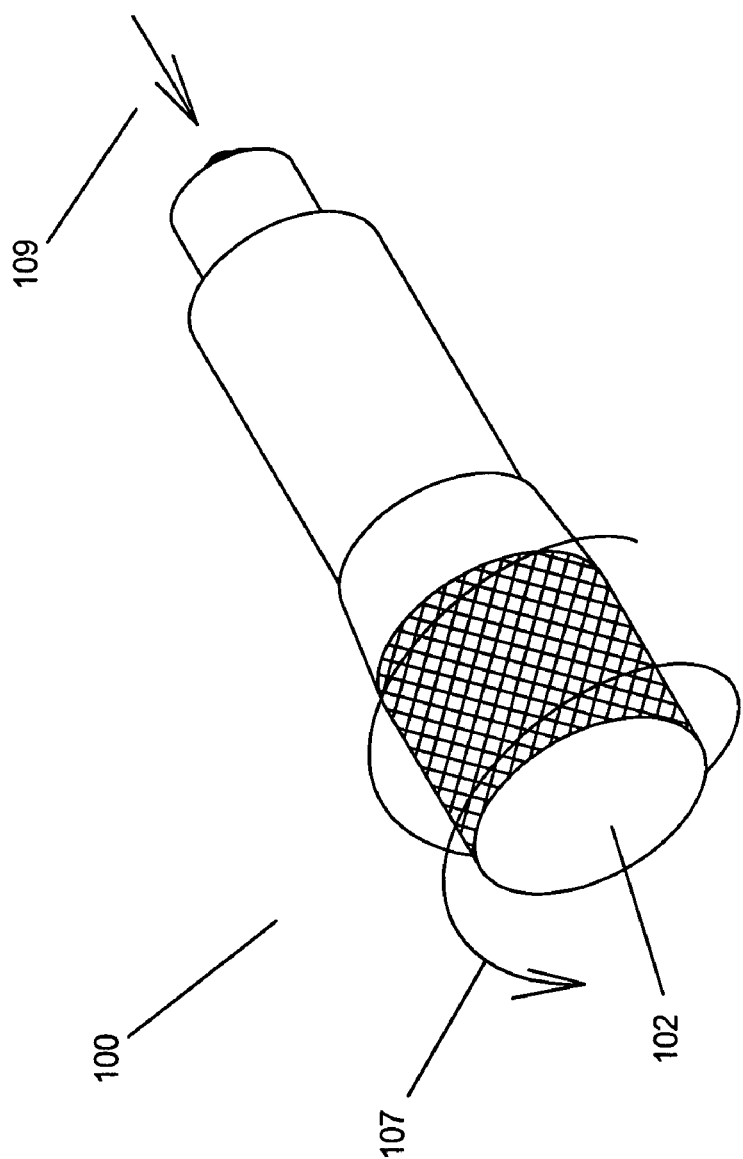
FIG. 23C is a perspective view that illustrates how the motor assembly rotates and translates in the reverse direction.

FIGS. 23A, 23B and 23C illustrate the motor assembly 100. FIG. 23A is a perspective view of motor assembly 100 reversed from FIG. 20. FIG. 23B illustrates operation of motor assembly 100 with the knob 102 and shaft 112 rotating clockwise 103 and translating in direction of arrow 105. By comparison, FIG. 23C illustrates operation of motor assembly 100 with the knob 102 and shaft 112 rotating counter clockwise 107 and translating in direction of arrow 109.

As will be apparent, and for the sake of simplicity of representation, the physical means of electrical connection to the various components of the motor assemblies have been omitted from the Figures.

As will also be apparent, the presence of the knurled knob 102 allows one to move the motor assembly 100 by manual means instead of or in addition to moving such motor assembly 100 by electrical means. Thus, e.g., the assembly 100 can be used as a micrometer drive replacement that will afford a user both the conventional means of manual adjustment as well as the additional means of electrically automated adjustment.

In one embodiment, not shown, knurled knob 102 is mechanically connected to an exterior motor to allow for a second means of mechanical movement of the assembly.

Figure 24A:
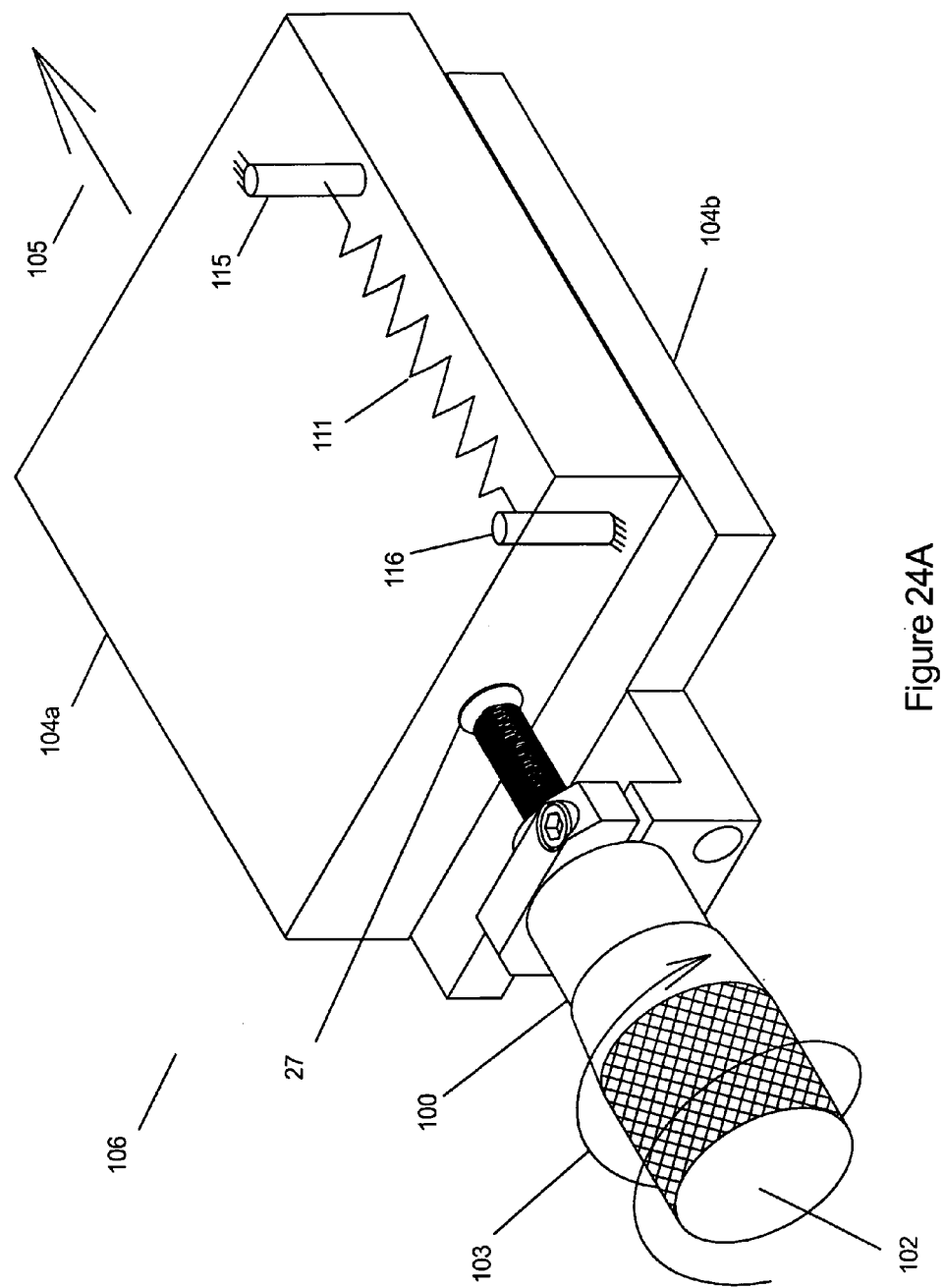
FIG. 24A shows the motor assembly integrated in a linear stage operating in the forward direction.
Figure 24B:
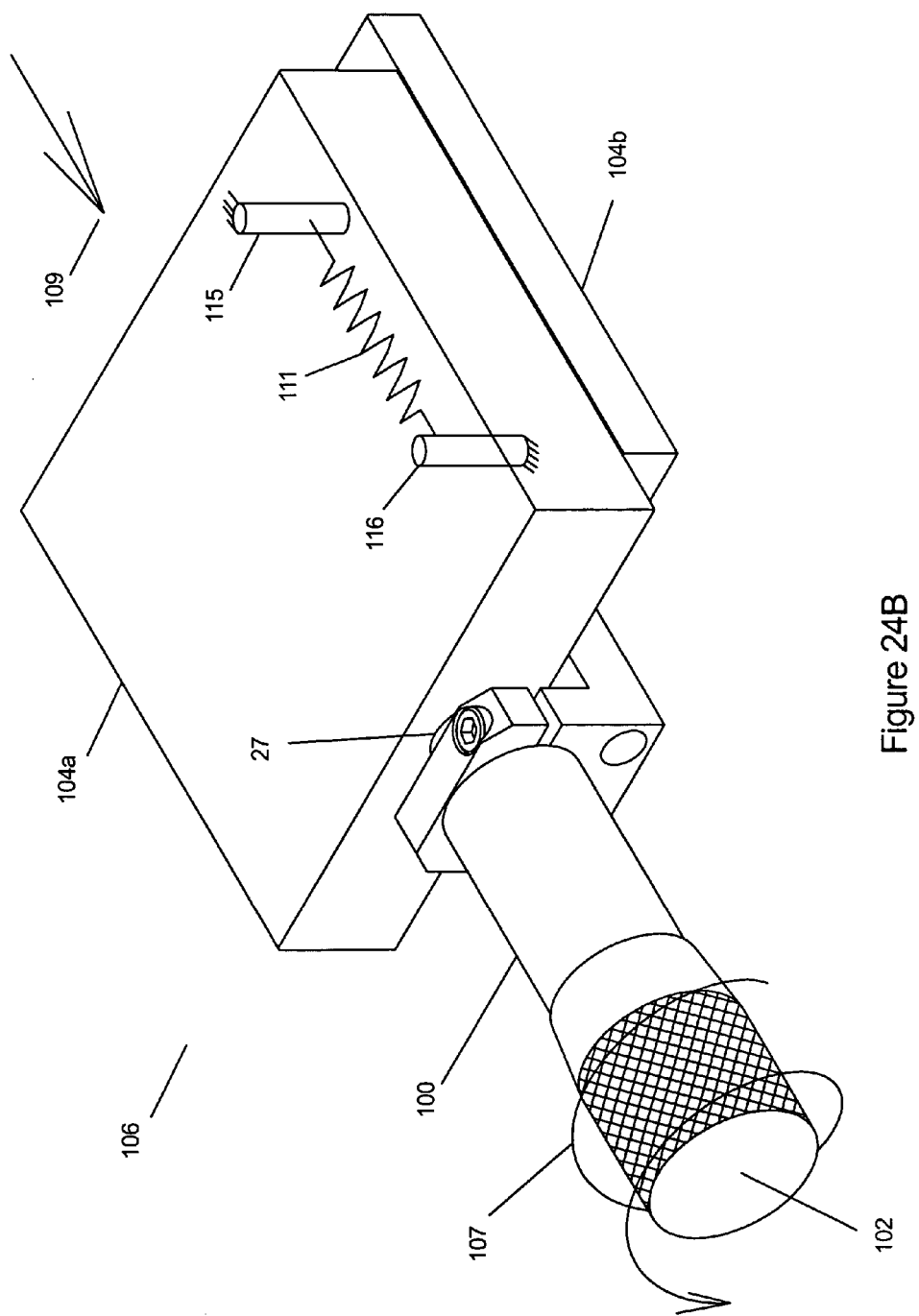

FIGS. 24A and 24B illustrate adjustable linear stages 106 that are comprised of motor assemblies 100 operatively connected to linear translation stages 104a/104b. In this embodiment cover 58 of motor assembly 100 is attached to the bottom stage portion 104b and ball 26 is in contact with top stage portion 104a. As will be apparent, when knurled knob 102 moves in clockwise in direction 103, linear motion in the direction of arrow 105 is produced. Conversely, when knurled knob 102 is move counterclockwise in direction 107, linear motion in the direction of arrow 109 is produced.

In one embodiment, illustrated schematically in FIGS. 24A and 24B, a spring assembly 111 comprised of pins 115 and 116 (shown in dotted line outline) biases translation stage 104a/104b in the direction of arrow 109. In the embodiment depicted, pin 115 is attached to the top, movable part 104a of the assembly, and the pin 116 is attached to the stationary bottom part 104b of the assembly. As will be apparent, the spring assembly 111 may be used to produce the axial force 27 (see FIGS. 5 and 6).

Figure 25:
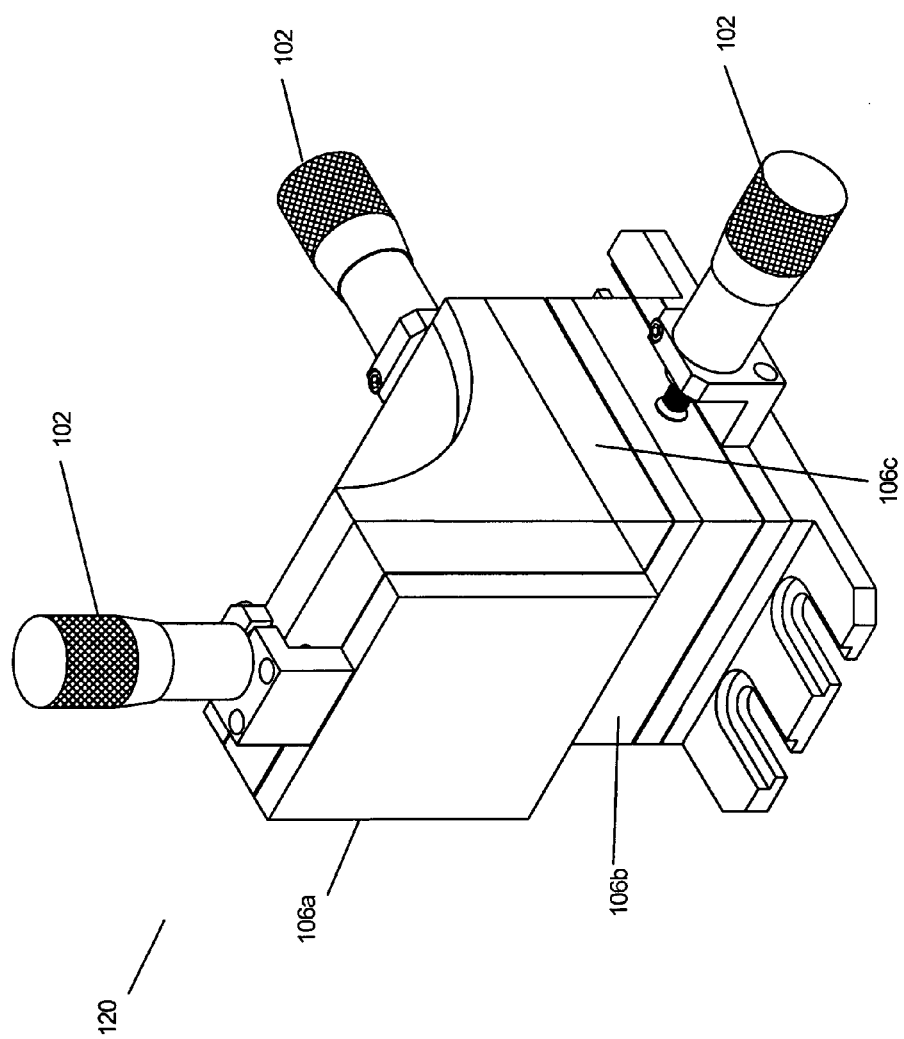
Figure 26:
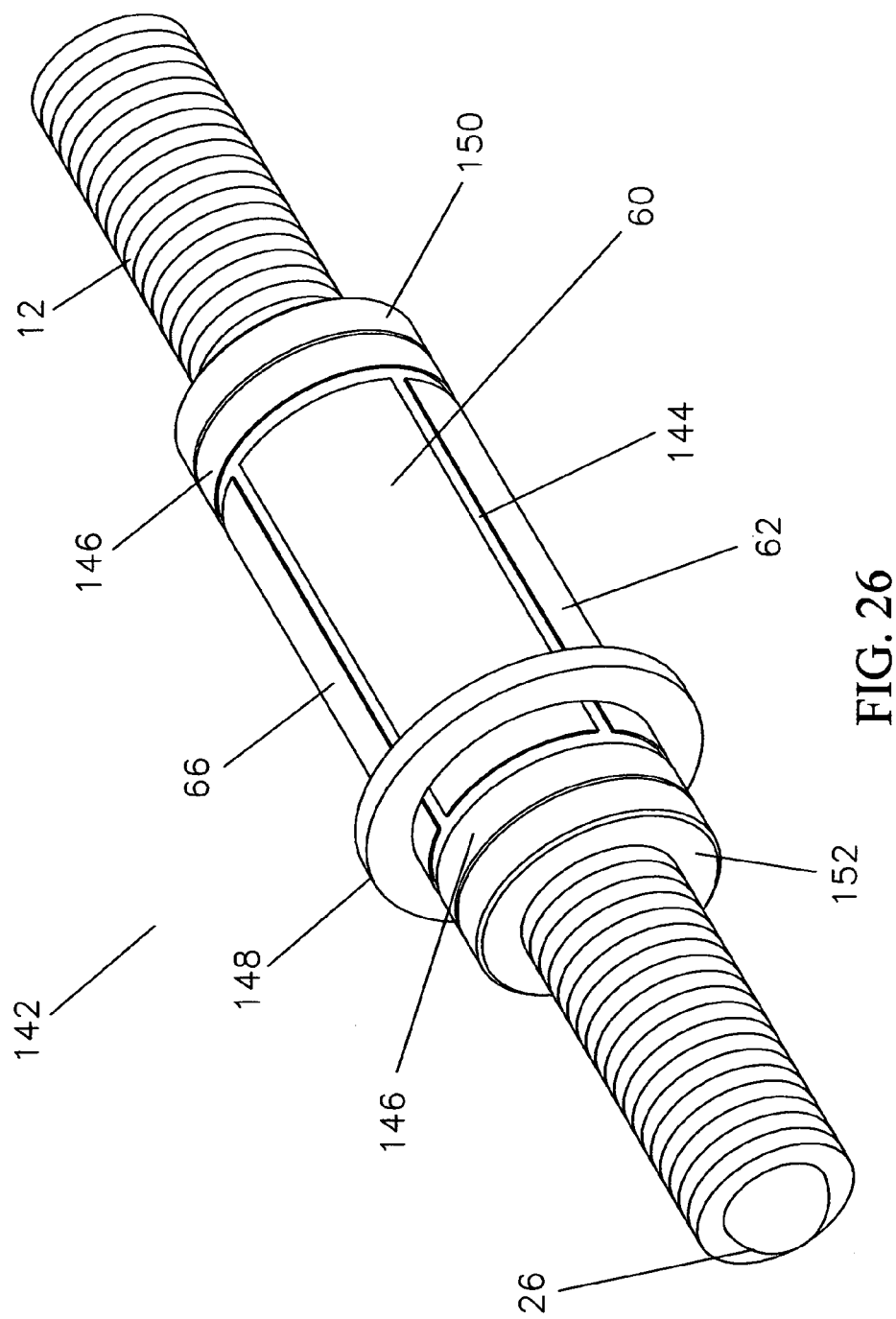
Figure 27:
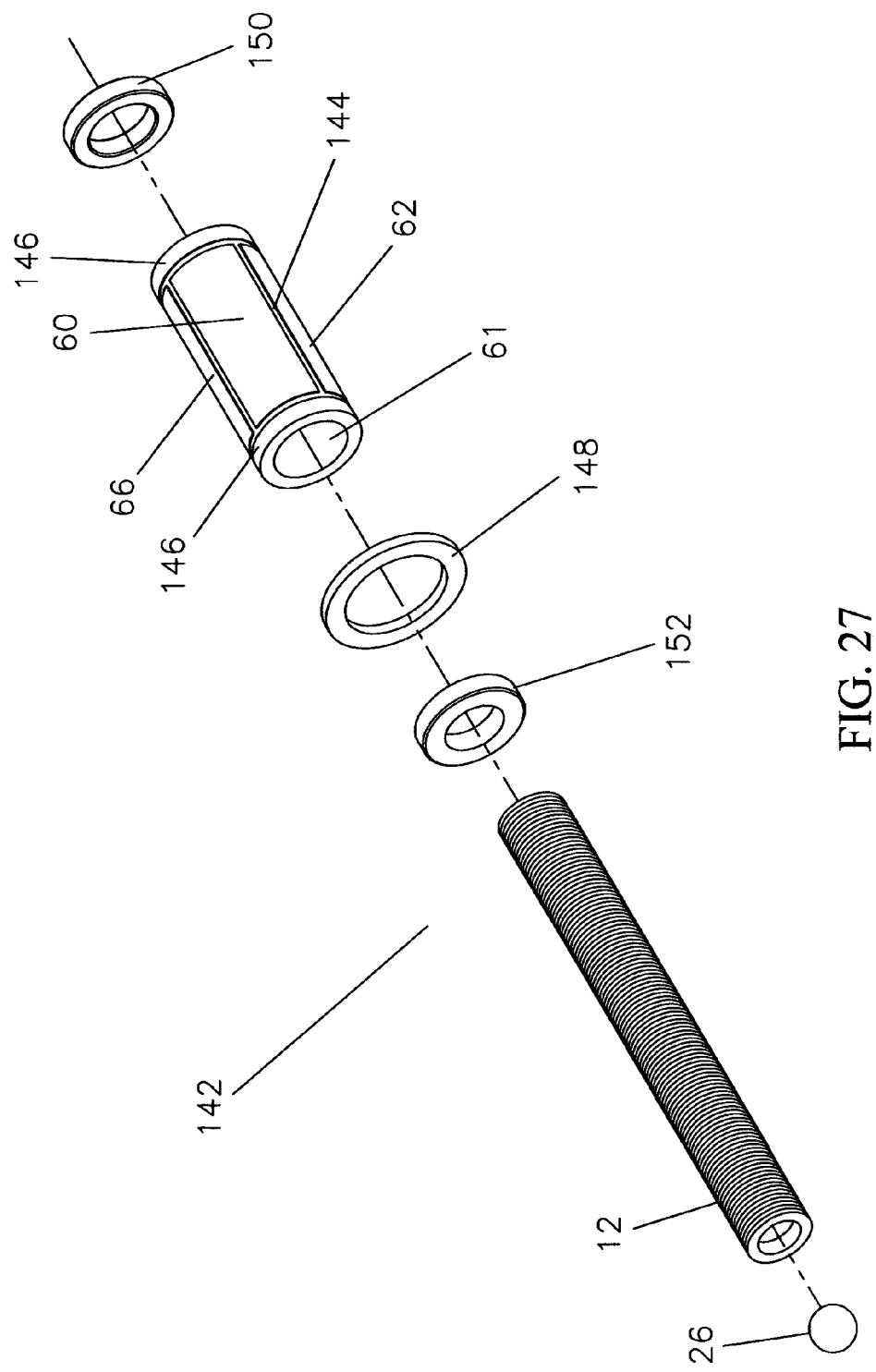
Figure 30:
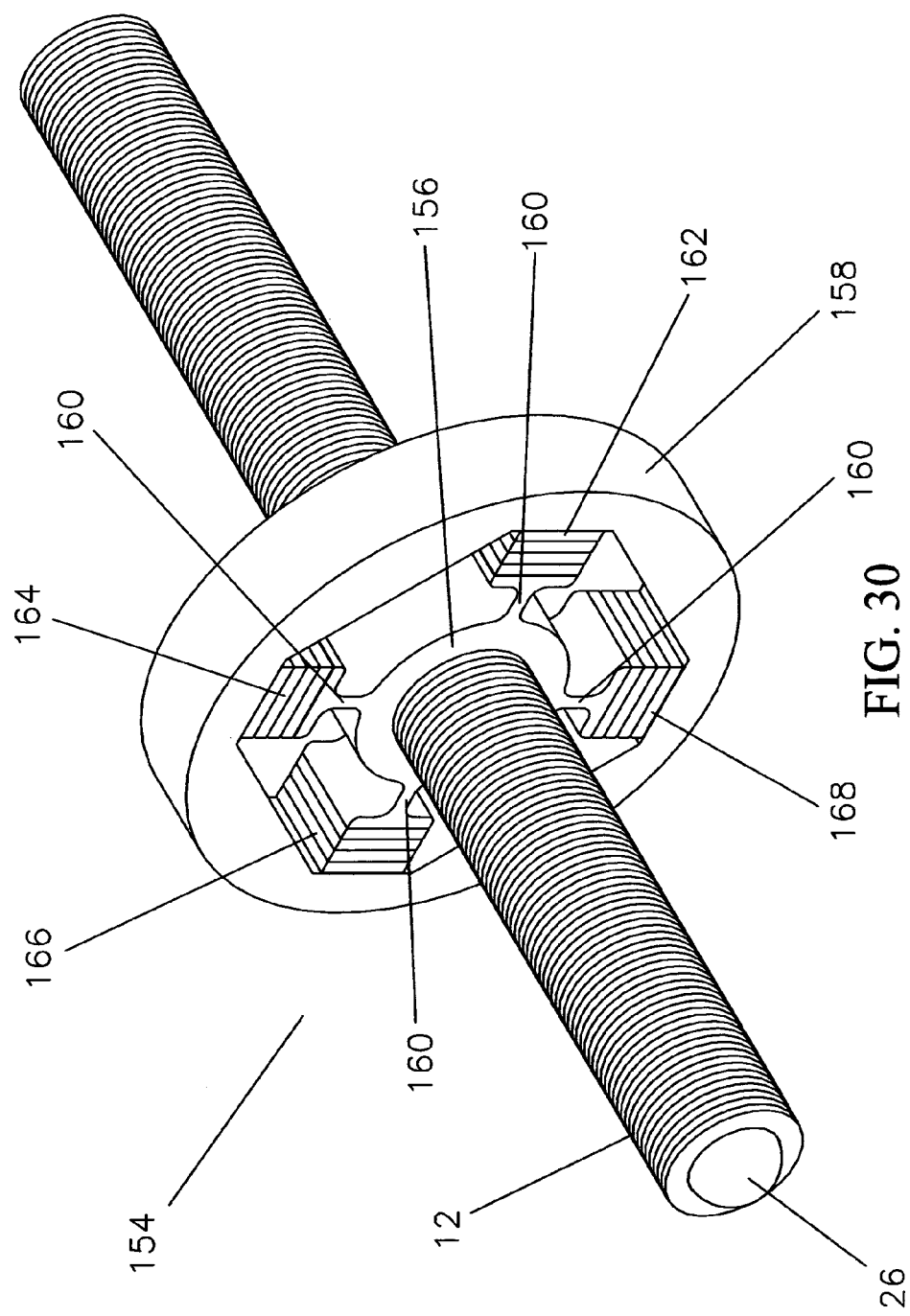
Figure 31:
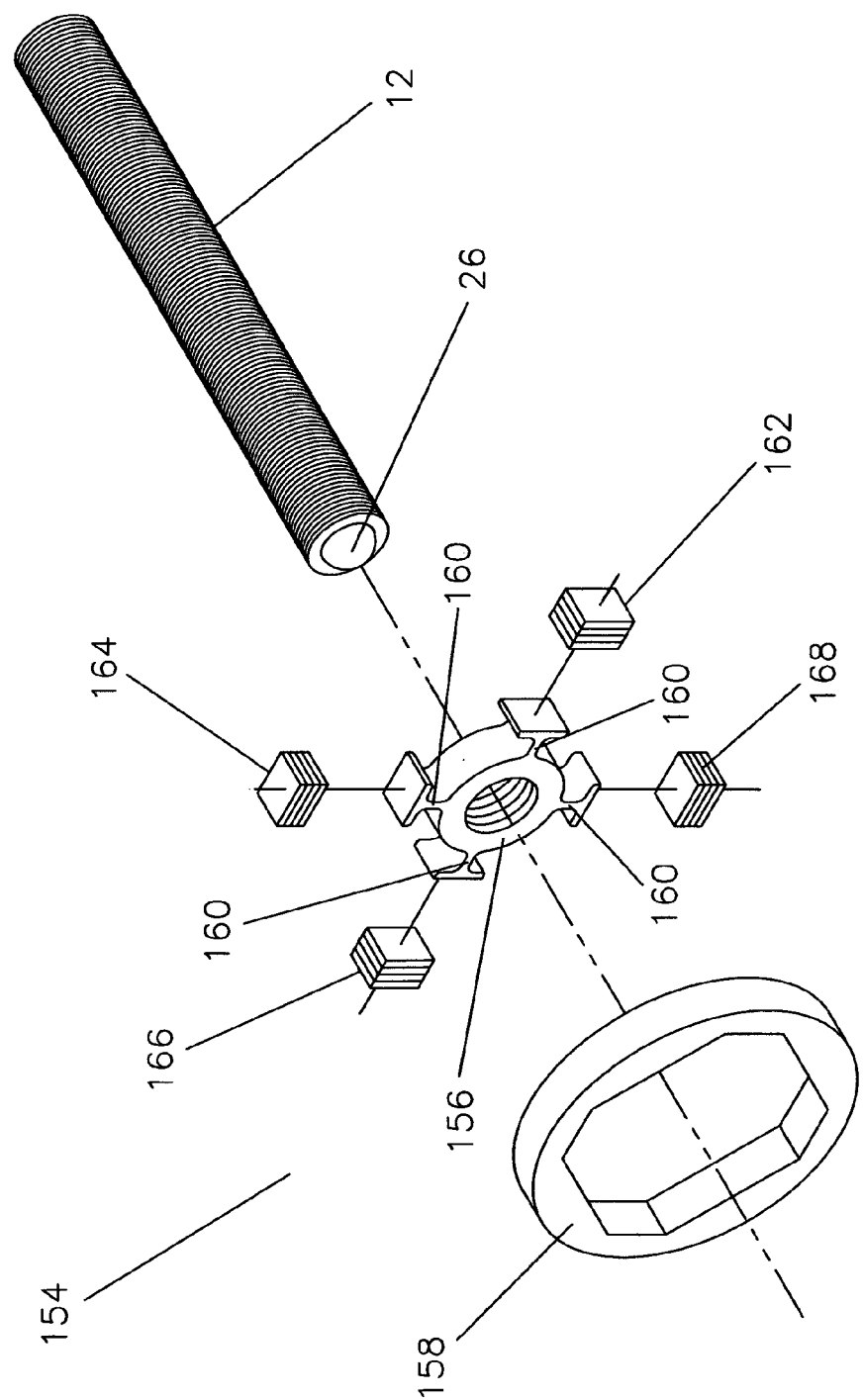
Figure 34:
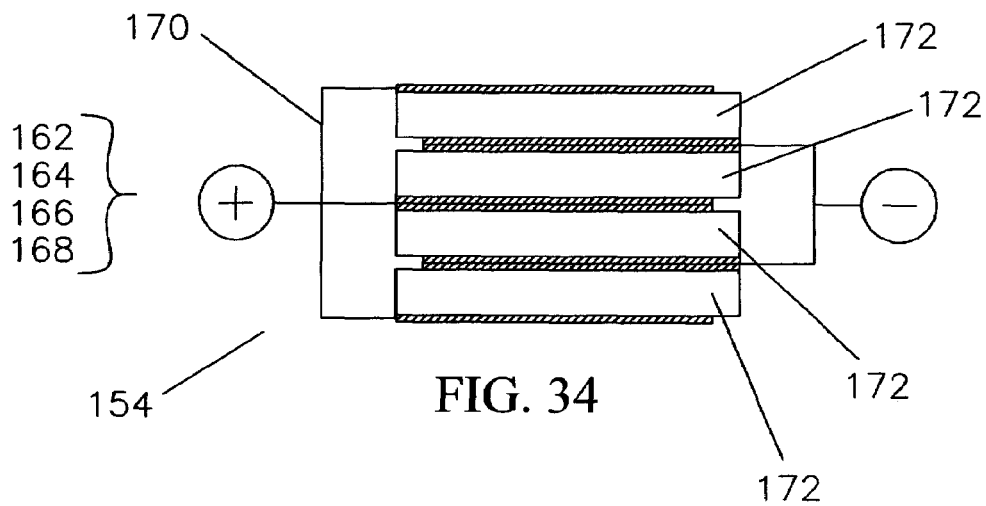
Figure 35:
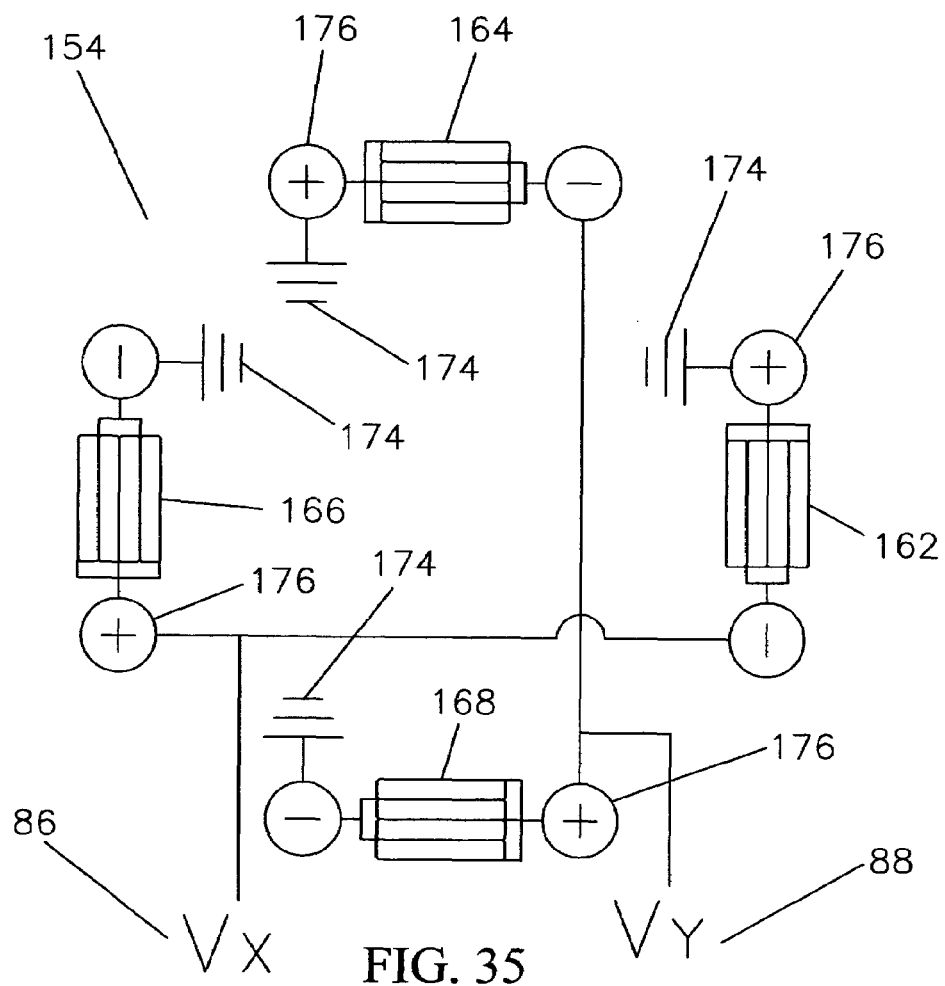

FIG. 25 is a perspective view of a micromanipulator 120 that is capable of moving its stages 106a, 106b, and 106c, in the X, Y, and Z axes.

Although the invention has been described in its preferred form with a certain degree of particularity, it is to be understood that the present disclosure of the preferred form can be changed in the details of construction, and that different combinations and arrangements of parts may be resorted to without departing form the spirit and the scope of the invention. In the previous portions of this specification, there has been described an apparatus for driving a threaded shaft assembly comprised of a threaded shaft with an axis of rotation and, engaged therewith, a threaded nut, wherein said assembly comprises means for subjecting said threaded nut to ultrasonic vibrations and thereby causing said shaft to simultaneously rotate and translate in the axial direction. As will be apparent, one may produce a comparable device that is comprised of means for causing said threaded shaft assembly to vibrate, thereby causing said threaded nut to simultaneously rotate and translate.

FIGS. 26 through 29 are schematics of another preferred motor 142 of the invention. Referring to FIGS. 26 through 29, the ultrasonic linear motor 142 uses a piezoelectric tube 144 with quadrant electrodes to generate ultrasonic vibrations. Motor 142 and tube 144 are similar to motor 50 and tube 54. (Refer to FIGS. 13 through 17.) A threaded shaft 12 with a spherical ball tip 26 rotates and produces axial force and motion. The rotation is produced by ultrasonic orbits of the threaded nut 152 connected to a vibrating piezoelectric tube 144. The inside diameter of the tube is a continuous electrode 61, which is grounded 63. The difference between tube 54 and tube 144 is electrode 61 wraps around the ends of the tube and forms an electrode ring 146 on the outside diameter of each end. The outside diameter of the tube is divided into four separate electrodes 60, 62, 64, and 66. The piezoelectric material is a commonly available "hard" composition with low dielectric losses and high depoling voltage. The axial length of the portion of the piezoelectric tube beneath each electrode 60, 62, 64, and 66 changes in proportion the applied voltage and the d31 piezoelectric charge coefficient. Electrode sections 60,64 and 62,66 work together in pairs respectively to bend the tube 144 and excite the orbital resonance. As previously discussed for motor 50, alternating electric drive signals 86 and 88 are applied to electrodes 60,64 and 62,66, respectively, with poling directions 43. For each electrode pair 60,64 and 62,66, the electric field is positive with respect to the poling direction on one electrode and negative with respect to the poling direction on the opposite electrode. Drive signal Vx 86 is applied to electrodes 60,64 and produces simultaneous expansion under one electrode and contraction under the opposite electrode; and thus it bends the tube in the X direction 72a/72b (see FIG. 18). In a similar manner the drive signal Vy 88 is applied to electrodes 62,66 and bends the tube in the Y direction 74a/74b (see FIG. 18).

Referring again to FIG. 26, the tube end opposite the threaded nut 152 is bonded to a guide bushing 150 with a small clearance between the bushing inside diameter and the outside diameter of the threaded shaft. The mounting flange 148 is bonded to the outside diameter of the tube 144 at the node point. The node point is the axial location on the tube that has minimum movement when the tube is resonating. The thread pitch on the shaft 12 and nut 152 converts the orbital tangential force and movement to axial force and movement. The pitch may be selected to optimize the force magnification, speed reduction, resolution enhancement and off-power holding force.

FIGS. 30 through 36 another preferred embodiment of the motor 154 of this invention. Referring to FIGS. 30 through 36, and in the preferred embodiment depicted therein, the ultrasonic linear motor 154 preferably uses four piezoelectric stacks 162, 164, 166 and 168 oriented radially in a plane at 90 degree spacing to generate ultrasonic vibrations. A threaded shaft 12 with a spherical ball tip 26 rotates and produces axial force and motion. The rotation is produced by an ultrasonic orbits of the threaded nut 156 connected to the four piezoelectric stacks 162, 164, 166, and 168 via elastic elements 160 where said stacks are bonded to the base flange 158. The four stacks 162 et seq. are constructed from piezoelectric plates 172 using well-established assembly and electrical interconnection methods 170 with the leads preferably being connected together to a common ground 174. The length of the stacks 162 et seq. changes in proportion to the applied voltage 69,70 and the d33 piezoelectric charge coefficient. The piezoelectric material is a commonly available "hard" composition with low dielectric losses and high depoling voltage. Alternating electrical drive signals 86 and 88 are connected to the leads of each piezoelectric stack and excite orbital vibrations of the nut. Piezoelectric stacks 162 et seq. work together in pairs, respectively, to move the nut 156 in an orbital resonance 76,78,80,82,84. Alternating electric drive signals Vx 86 and Vy 88 are applied to stacks 162,166 and 164,168 respectively, with poling directions 176. For each stack pair 162,166 and 164,168 the electric field is positive with respect to the poling direction 176 on one stack and negative with respect to the poling direction on the opposite stack. Drive signal Vx 86 is applied to stacks 162,166 and produces simultaneous expansion on one stack and contraction on the opposite stack; and thus it translates the nut 156 in the X direction 72a/72b. In a similar manner, the drive signal Vy 88 is applied to stacks 164,168 and translates the nut 156 in the Y direction 74a/74b. While not shown, it is understood by those skilled in the art that actuator configurations, other than piezoelectric stacks 162 et seq., may also be used to produce the same orbital resonance of nut 156. Such actuators include piezoelectric plates that change length in proportion the applied voltage and the d31 piezoelectric charge coefficient, electromagnetic solenoids or voice coils, electrostatic attraction, or other tranducers capable of producing ultrasonic frequency motion. The thread pitch on the shaft 12 and nut 156 converts the orbital tangential force and movement to axial force and movement. The pitch may be selected to optimize the force magnification, speed reduction, resolution enhancement and off-power holding force.

FIGS. 37 through 39 illustrate an optical assembly 180 that is comprised of one of the motors 142 of this invention. As will be apparent from these Figures, in the emobodiment depicted the lens 184 is rotationally symmetric with its centerline 204 coincident with 204 axis of rotation of the threaded hollow shaft 182.

Referring to FIGS. 37 through 39 and in the preferred embodiment depicted therein, the optical alignment mechanism 180 integrates a motor 142 with a shaft 182 that has a hollow center with an optical element 184 aligned and bonded on the shaft centerline 204. The optical element 184 can be of many types including transmissive, reflective, concave, convex or assemblies of multiple optical elements. The motor 142 causes the hollow shaft 182 and optical element 184 to rotate and translate 202 achieving precise optical alignment for functions such changing focal length or focusing.

In the embodiment depicted in FIGS. 37 through 39, an optical element 184 is used. In this embodiment, the optical element is a lens. It is preferred that the optical element 184 be a movable optical element. One may use many of the movable optical elements known to those skilled in the art. Reference may be had, e.g., to U.S. Pat. Nos. 3,612,664 (optical path compensating device), 3,958,117 (distance determining and automatic focusing apparatus), 4,184,759 (photographic apparatus), 4,629,308 (lens and shutter positioning mechanism for variable magnification copier), 5,296,943 (multi-path electronic camera assembly), 5,894,371 (focus mechanism for varifocal lens), 5,969,886 (lens barrel and optical apparatus), 6,236,448 (projection exposure system), 6,445,514 (micro-positioning optical element), 6,606,426 (beam alignment systems), 6,678,240, and the like. The disclosure of each of these United States patent applications is hereby incorporated by reference into this specification.

By way of further illustration, one may use one or more of the linear motors of this invention in prior art cameras that utilize prior art motors. Thus, by way of illustration, one may replace the prior art motor in one or more of the cameras described in U.S. Pat. Nos. 5,091,781 (camera moving apparatus), 5,157,435 (automatic focusing apparatus for a video camera), 5,357,308 (automatic zoom camera and driving method thereof), 5,434,621 (object tracing device for automatic zooming), 5,943,513 (camera zooming apparatus), and the like. The entire disclosure of each of these United States patents is hereby incorporated by reference into this specification.

FIGS. 40 through 42 illustrate another preferred optical assembly 186. Referring to FIGS. 40 through 42 and in the preferred embodiment depicted therein, the optical alignment mechanism 186 integrates a motor 154 with a shaft 182 that has a hollow center with an optical element 184 aligned and bonded on the shaft centerline. The optical element 184 can be of many types including transmission, reflective, concave, convex or assemblies of multiple optical elements. The motor 154 causes the hollow shaft 182 and optical element 184 to rotate and translate 202 on centerline 204 achieving precise optical alignment for functions such changing focal length or focusing.

FIGS. 43 through 45 illustrate yet another preferred optical assembly 188. Referring to FIGS. 43 through 45 and in the preferred embodiment depicted therein, a camera auto-focus and auto-zoom assembly 188 integrates two optical alignment mechanisms 194 and 196, similar to mechanism 186, with a focal plane imaging device 192 such as a CCD array and housing 190. Mechanism 196 is closest to the imaging device 192 and incorporates a transmission lens that changes the camera zoom by translating the lens 198 relative to device 192 and lens 200. In this embodiment the zoom lens 198 diameter is larger than the imaging device 192 and focus lens 200 so that mechanism 196 can translate without interference. Mechanism 194 is adjacent to mechanism 196, opposite device 192, and incorporates a transmission lens that changes the camera focus by translating the lens 200 relative to lens 198 and device 192. In this embodiment the diameter of the focus lens 200 is smaller than the zoom lens 198 to eliminate interference when translating mechanism 194. The centerlines of optical elements 198 and 200 are coincident with centerline 204 and perpendicular to the image plane of device 192. Elements 198 and 200 translate and rotate 202 simultaneously. In this embodiment, elements 198 and 200 are rotationally symmetric around centerline 204.

Figure 48:
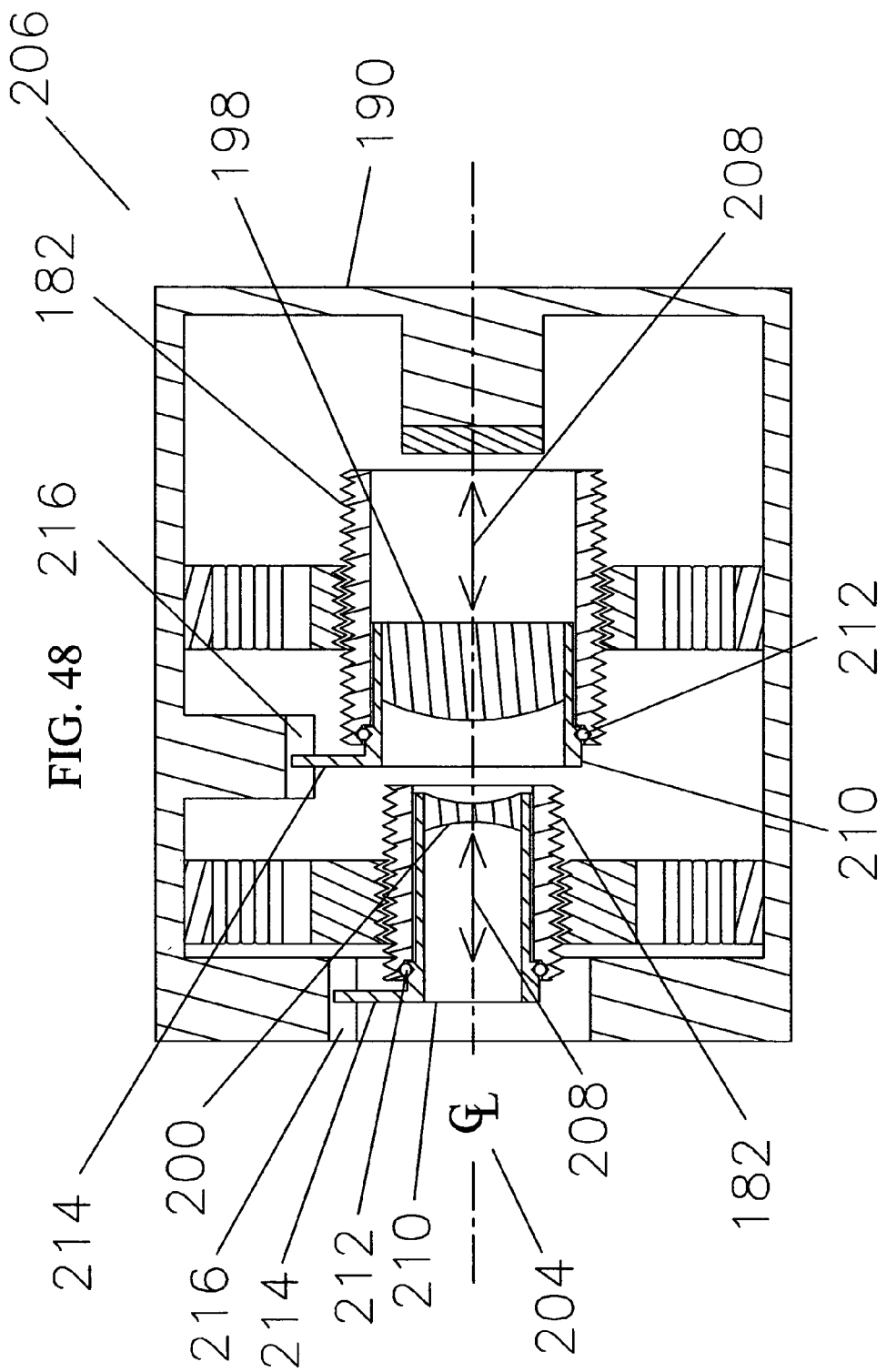

FIGS. 46 through 48 illustrate yet another preferred optical assembly 206. Referring to FIGS. 46 through 48, and in the preferred embodiment depicted therein, a camera auto-focus and auto-zoom assembly 206 with translating 208 but non-rotating optical lens 198 and 200 is described for situations where non-rotating optics is required. Said assembly 206 is similar to assembly 188 with translating and rotating 202 optical lens 198 and 200 but incorporates lens mounting shafts 210 that are connected to the threaded motor shafts 182 via a low friction rotary bearing 212 such as a ball bearing. A pin 214 is connected to the end of each mounting shaft 210 and oriented perpendicular to centerline 204. Said pin 214 engages a stationary slot 216 in housing 190 which prevents rotation of the pin 214, mounting shaft 210 and lens 198 and 200 but allows translation of the pin 214, mounting shaft 210 and lens 198 and 200 in the axial direction 208 parallel to centerline 204.

As will be apparent to those skilled in the art, the optical assemblies illustrated in FIGS. 26 through 48 are merely illustrative of the many movable optical elements with which applicant's linear motor may be utilized.

The invention having been fully described, it will be apparent to those skilled in the art that many changes and modifications may be made thereto without departing from the spirit and scope of the appended claims.

I claim:

1. An optical assembly comprised of an optical device movably attached to an apparatus for driving a threaded shaft assembly, wherein said apparatus is comprised of a threaded shaft with an axis of rotation and, engaged therewith, a threaded nut, wherein said assembly comprises means for subjecting said threaded nut to ultrasonic vibrations and thereby causing said threaded shaft to simultaneously rotate and translate in the axial direction.

2. The optical assembly as recited in claim 1, wherein said optical device is attached to said threaded shaft.

3. The optical assembly as recited in claim 2, wherein said optical device is comprised of a lens.

4. The optical assembly as recited in claim 3, wherein said shaft is a threaded hollow shaft, and said lens is mounted within said threaded hollow shaft.

5. The optical assembly as recited in claim 4, wherein said lens is rotationally symmetric with its centerline coincident with said axis of rotation of said threaded hollow shaft.

6. The optical assembly as recited in claim 5, wherein said apparatus comprises means for moving said threaded nut in an orbital direction.

7. The optical assembly as recited in claim 6, wherein said threaded nut is a substantially rigid body.

8. The optical assembly as recited in claim 7, further comprising a housing in which said threaded shaft assembly is disposed.

9. The optical assembly as recited in claim 8, wherein said assembly is comprised of a piezoelectric tube.

10. The optical assembly as recited in claim 9, wherein said piezoelectric tube has a first bending resonant frequency in excess of 20,000 cycles per second, and wherein the first bending mode lies in a plane parallel to said axis of rotation.

11. The optical assembly as recited in claim 8, wherein said assembly is comprised of four piezoelectric stacks and elastic elements, wherein said elastic elements are connected to said threaded nut.

12. The optical assembly as recited in claim 11, wherein said four piezoelectric stacks have a first bending resonant frequency in excess of 20,000 cycles per second.

13. The apparatus as recited in claim 10, wherein said housing has a second bending resonant frequency that is identical to said first bending resonant frequency, and wherein the second bending mode lies in a plane orthogonal to said first bending mode.

14. The apparatus as recited in claim 1, further comprising means for orbiting said threaded nut at a frequency of at least about 20,000 orbits per second.

15. The apparatus as recited in claim 14 wherein said means for orbiting said threaded nut is comprised of at least two transducers for changing electrical energy into force.

16. The apparatus as recited in claim 15 wherein said transducers are selected from the group consisting of piezoelectric transducers, electrostrictive transducers, magnetostrictive transducers, electostatic transducers, electromagnetic transducers, and mixtures thereof.

17. A camera comprised of a first optical assembly, a second optical assembly, and a focal plane imaging device, wherein:
  (a) said first optical assembly is comprised of a first optical device movably attached to a first apparatus for driving a first threaded shaft assembly, wherein said first apparatus is comprised of a first threaded shaft with a first axis of rotation and, engaged therewith, a first threaded nut, wherein said first assembly comprises first means for subjecting said first threaded nut to ultrasonic vibrations and thereby causing said first threaded shaft to simultaneously rotate and translate in the axial direction,
  (b) said second optical assembly is comprised of a second optical device movably attached to a second apparatus for driving a second threaded shaft assembly, wherein said second apparatus is comprised of a second threaded shaft with a second axis of rotation and, engaged therewith, a second threaded nut, wherein said second assembly comprises second means for subjecting said second threaded nut to ultrasonic vibrations and thereby causing said second threaded shaft to simultaneously rotate and translate in the axial direction; and
  (c) said focal plane imaging device is optically connected to said first optical assembly and said second optical assembly.

18. The camera as recited in claim 17, wherein said first axis of rotation and said second axis of rotation coincident, and wherein said focal plane of said focal plane imaging device is substantially perpendicular to said first axis of rotation and said second axis of rotation.

19. The camera as recited in claim 18, wherein said first optical assembly is a zoom optical assembly, and wherein said second optical assembly is a focus optical assembly.

20. The optical assembly as recited in claim 4, further comprising means for allowing said lens to translate while preventing such lens from rotating.

* * * * *